(12) United States Patent
Peter et al.

(10) Patent No.: US 11,350,955 B2
(45) Date of Patent: Jun. 7, 2022

(54) INTRAVASCULAR ARTICULATING RETRIEVAL APPARATUS

(71) Applicant: First Pass, LLC, Paradise Valley, AZ (US)

(72) Inventors: Sunenshine J. Peter, Paradise Valley, AZ (US); Kevin Hirsch, Phoenix, AZ (US); Joseph Barrett, Tempe, AZ (US)

(73) Assignee: First Pass, LLC, Paradise Valley, AZ (US)

( * ) Notice: Subject to any disclaimer, the term of this patent is extended or adjusted under 35 U.S.C. 154(b) by 0 days.

(21) Appl. No.: 17/292,014

(22) PCT Filed: Sep. 14, 2020

(86) PCT No.: PCT/US2020/050711
§ 371 (c)(1),
(2) Date: May 7, 2021

(87) PCT Pub. No.: WO2021/051075
PCT Pub. Date: Mar. 18, 2021

(65) Prior Publication Data
US 2021/0315600 A1    Oct. 14, 2021

Related U.S. Application Data

(60) Provisional application No. 62/899,180, filed on Sep. 12, 2019.

(51) Int. Cl.
*A61B 17/22* (2006.01)
*A61B 17/295* (2006.01)
(Continued)

(52) U.S. Cl.
CPC ...... *A61B 17/22031* (2013.01); *A61B 17/295* (2013.01); *A61F 2/95* (2013.01);
(Continued)

(58) Field of Classification Search
CPC ............ A61B 17/22031; A61B 17/221; A61B 2017/22035; A61B 2017/2908;
(Continued)

(56) References Cited

U.S. PATENT DOCUMENTS 5,474,057 A    12/1995   Makower et al.
5,486,189 A    1/1996    Mudry et al.
(Continued)

*Primary Examiner* — Wade Miles
(74) *Attorney, Agent, or Firm* — Invention To Patent Services; Alex Hobson

(57) ABSTRACT

An intravascular articulating retrieval apparatus may be used to move objects within the vasculature, such as to remove an intravascular filter, tissue and other items from the vasculature. The apparatus has a user interface to manipulate a first and second actuating portion that are coupled to the distal end of the apparatus conduit. A retrieval apparatus may include forceps coupled to the second actuating portion whereby the retrieval actuator opens and closes the forceps for retrieval of an IVF or other device, such as stent or stent graft. An intravascular articulating retrieval apparatus may be used to dissect thrombus from the interior of the vascular wall, move a stent or remove a portion of a stent or stent graft to provide better blood flow or to allow blood flow into a branched vessel.

24 Claims, 20 Drawing Sheets

(51) Int. Cl.
*A61F 2/95* (2013.01)
*A61F 2/01* (2006.01)

(52) U.S. Cl.
CPC ....... *A61F 2/011* (2020.05); *A61F 2002/9528* (2013.01); *A61F 2002/9534* (2013.01)

(58) Field of Classification Search
CPC .............. A61F 2/011; A61F 2002/9528; A61F 2002/9534; A61M 25/0133; A61M 25/0136; A61M 25/0147; A61M 2025/015
See application file for complete search history.

(56) References Cited

U.S. PATENT DOCUMENTS

| | | | |
|---|---|---|---|
| 2003/0069598 A1 | 4/2003 | Miser | |
| 2004/0242960 A1 | 12/2004 | Orban, III | |
| 2011/0087269 A1 | 4/2011 | Stokes et al. | |
| 2011/0152922 A1* | 6/2011 | Jeong | A61B 17/2909 606/205 |
| 2012/0035617 A1 | 2/2012 | Joshi et al. | |
| 2012/0277762 A1* | 11/2012 | Lathrop | A61B 34/70 606/130 |
| 2013/0090714 A1 | 4/2013 | McHugo | |
| 2015/0230811 A1 | 8/2015 | Kovarik et al. | |
| 2016/0228134 A1 | 8/2016 | Martin et al. | |
| 2016/0243697 A1* | 8/2016 | Sato | A61B 34/70 |
| 2016/0256183 A1 | 9/2016 | Cooper | |
| 2017/0000507 A1 | 1/2017 | Conlon et al. | |
| 2017/0319200 A1 | 11/2017 | Nicholas | |
| 2018/0001058 A1* | 1/2018 | Schlesinger | A61B 34/74 |
| 2019/0090963 A1* | 3/2019 | Canady | A61B 34/74 |
| 2019/0274781 A1* | 9/2019 | Lambrecht | B08B 9/032 |
| 2020/0375677 A1* | 12/2020 | Genova | A61B 34/71 |

* cited by examiner

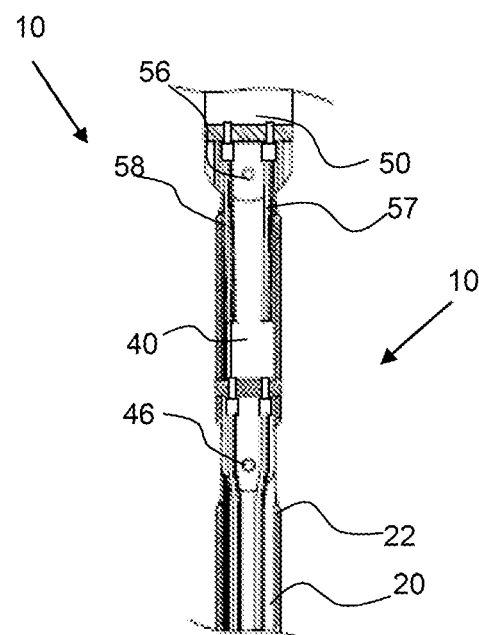
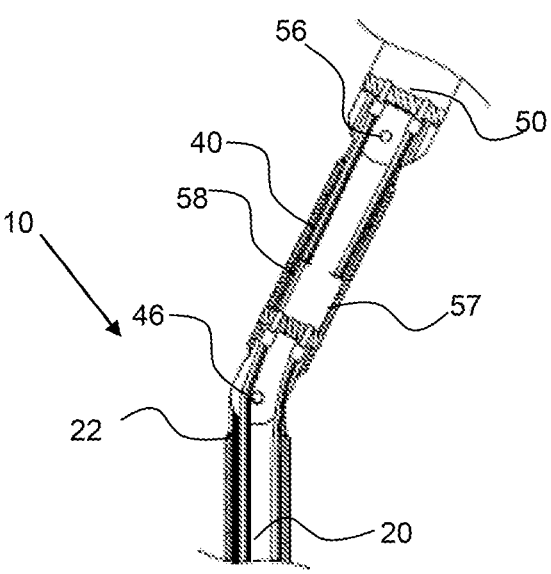
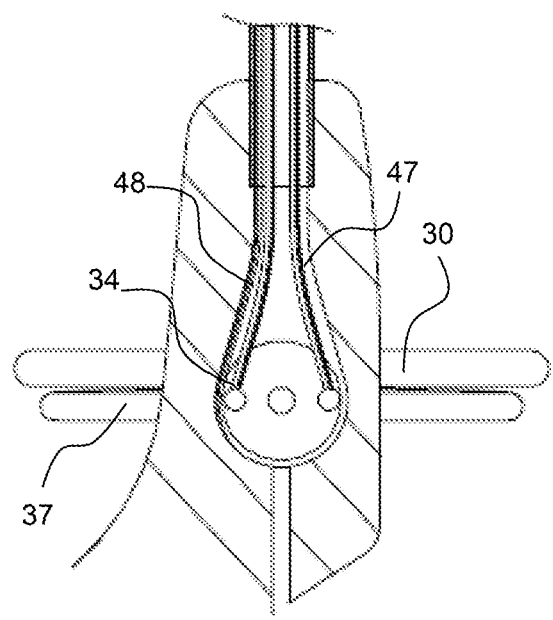
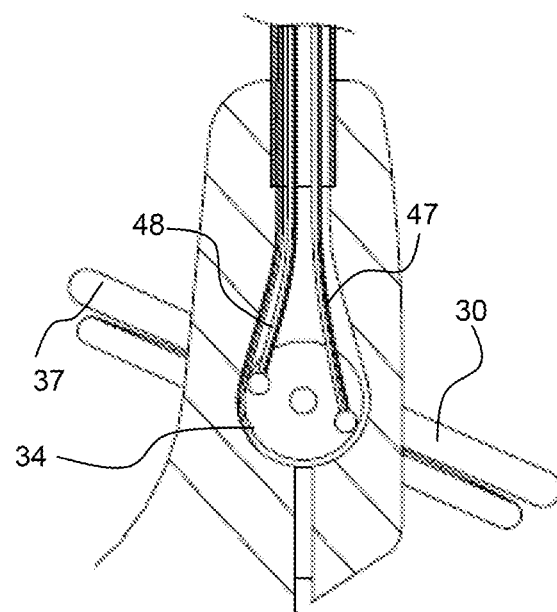
FIG. 19  FIG. 20

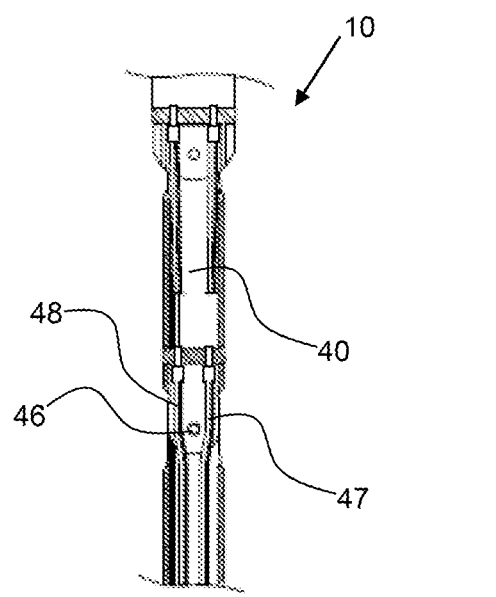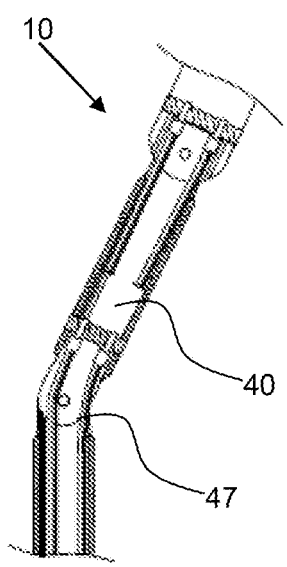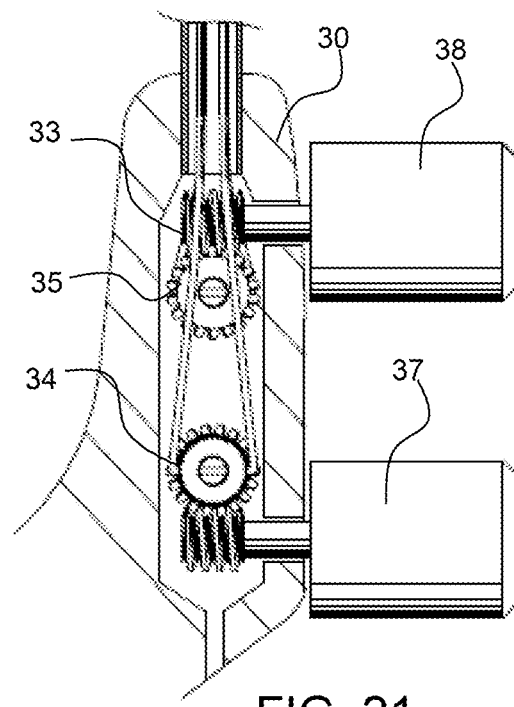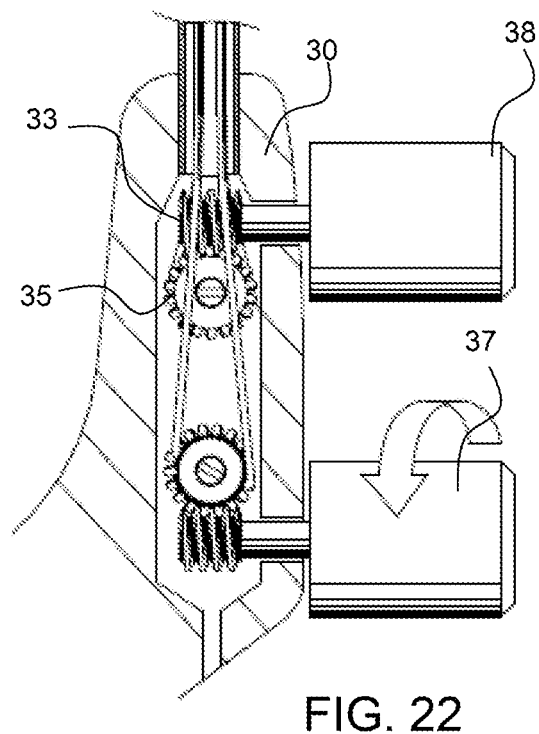
FIG. 21          FIG. 22

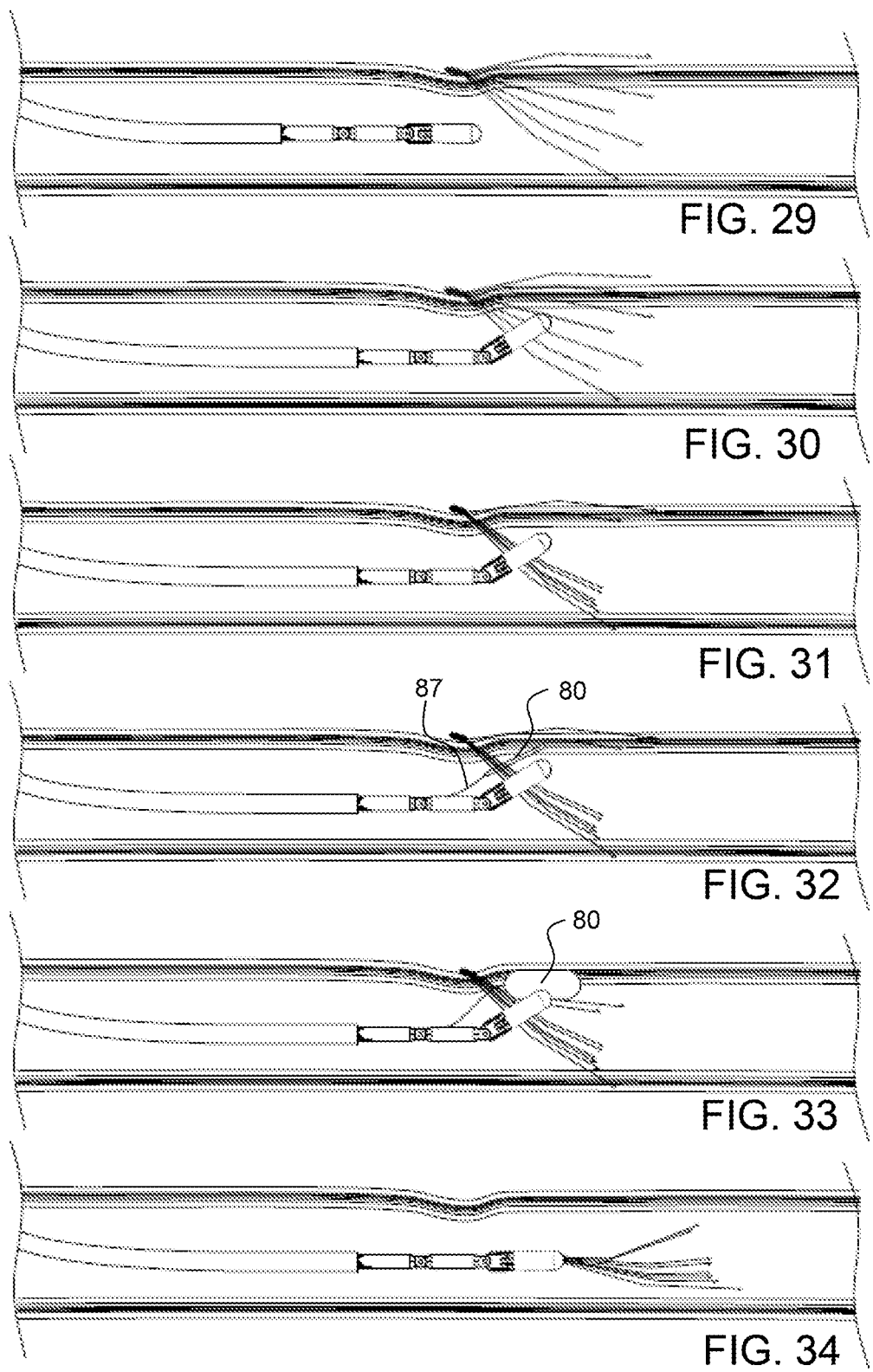

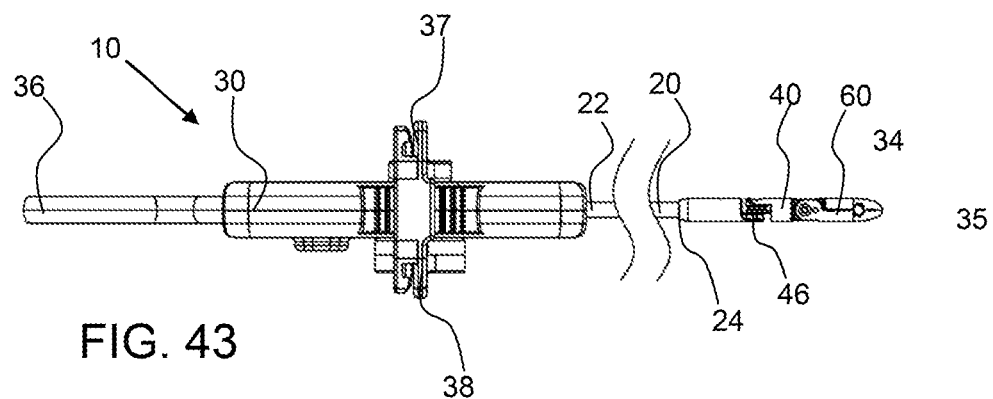
FIG. 43
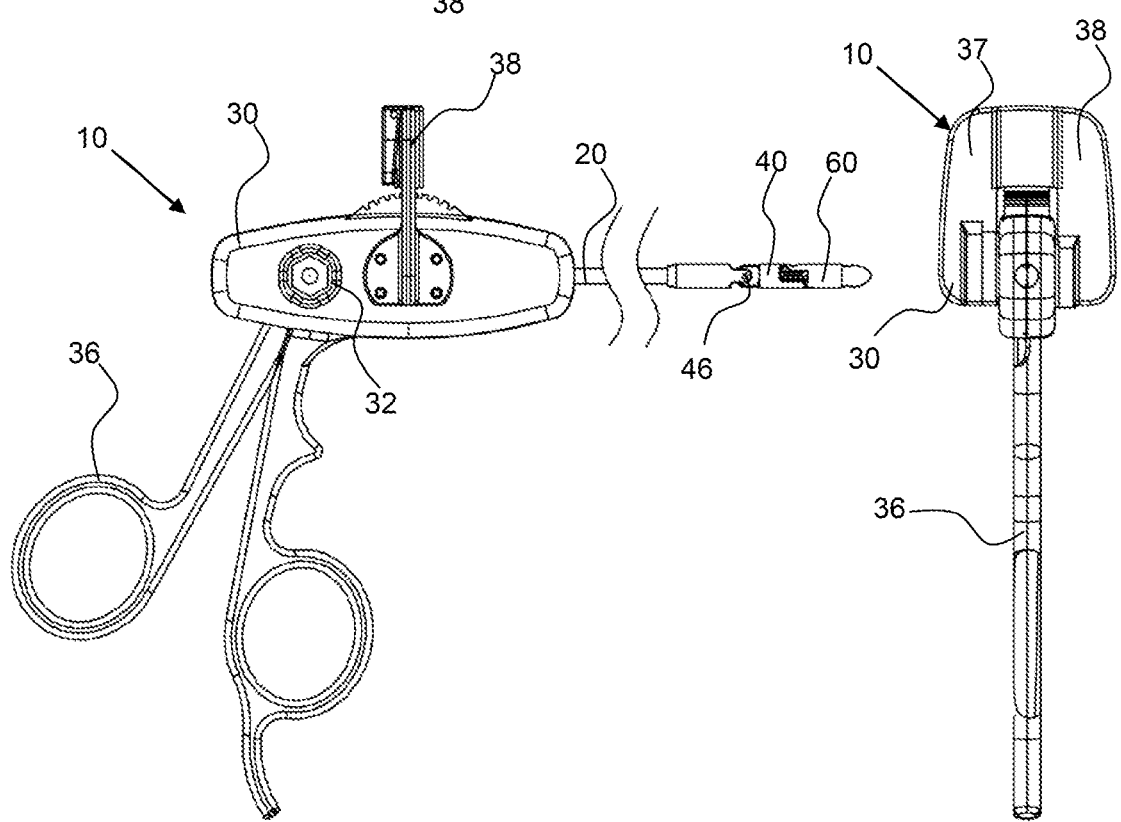
FIG. 44
FIG. 45

INTRAVASCULAR ARTICULATING RETRIEVAL APPARATUS

CROSS REFERENCE TO RELATED APPLICATIONS

This application claims the benefit of priority to U.S. provisional patent application No. 62,899,180, filed on Sep. 12, 2019; the entirety of which is hereby incorporated by reference herein.

BACKGROUND OF THE INVENTION

Field of the Invention

The invention relates to an intravascular articulating retrieval apparatus that is an externally and mechanically controlled manipulator and methods of using to move or remove an intravascular filter or foreign body, as well as visualize, cut, grind, ablate, remodel or otherwise manipulate or examine the vascular tissue from inside the vasculature.

Background

One of the more commonly placed intravascular devices that is meant to be retrieved is the retrievable inferior vena cava filter. Inferior vena cava (IVC) filters or intravascular filters (IVF) are primarily placed in the inferior vena cava to trap pathologic venous emboli to reduce the risk of a pulmonary embolism. Currently there are a number of iterations of retrieval devices for these filters, each of which has its own type of retrieval mechanism. Most commonly, the mechanism of retrieval includes the snaring or capturing of a hook at the apex of the filter and then advancing a sheath over the filter to re-constrain and capture the legs and distal hooks that keep the filter in place. Once snared, the filter is fixed by the snare, while a vascular sheath is "slid" over the filter in order to dissect from the vessel wall, and remove the device through a relatively small diameter vascular sheath.

Ideally all filters that are placed would be removed when they are no longer required by the patient's clinical condition. There are many issues with the current method of removing these IVF's. It is often difficult to snare the various hooks on the devices, and the snare is not easily directed or deployed. Additionally, these filters not infrequently become tilted and the apex becomes lodged into, or extends completely through, the vessel wall, making them extremely difficult to retrieve with existing methods and devices. Over time, tissue overgrowth alone causes the filter or foreign body to become more embedded in the inferior vena cava. A large amount of force is required to remove the device, which is not possible through standard catheter/snare retrieval mechanisms. The current retrieval mechanisms do not allow the freedom of motion to direct catheter/snare to one side of the vessel wall or the other.

Other vascular implants such as cardiac pacer leads, stents, or unintentionally deposited foreign bodies such as coils or wires, also can be very difficult to remove with existing devices for the same reasons as stated above.

SUMMARY OF THE INVENTION

The invention is directed to an intravascular articulating retrieval apparatus that is an externally and mechanically controlled, intravascular articulating manipulator and methods of using to remove an intravascular filter or foreign body, as well as visualize, cut, grind, ablate, remodel or otherwise manipulate or examine the vascular tissue from inside the vasculature.

An exemplary intravascular articulating retrieval apparatus has a user interface to manipulate a first actuating portion about a first pivot and in some embodiments a second actuating portion about a second pivot. The actuating portion (s) are coupled to the distal end of the apparatus conduit. The actuating portions may rotate in the same or at an offset angle to each other, such as in orthogonal directions with respect to each other. An exemplary intravascular articulating retrieval apparatus is an articulating retrieval apparatus that has forceps coupled to an actuating portion and is controlled by a retrieval actuator that opens and closes the forceps for retrieval of an IVF or other device or dissection of tissue or devices, such as stents or stent grafts. An exemplary intravascular articulating retrieval apparatus may be used to dissect thrombus from the interior of the vascular wall, move or reposition a stent or stent graft or remove a portion of a stent or stent graft to provide better blood flow or to allow blood flow into a branched vessel. An exemplary intravascular articulating retrieval apparatus may be used to retrieve any foreign body or move, reposition or dissect biological tissue within the body.

An exemplary intravascular articulating retrieval apparatus has a first actuating portion configured distal from the user interface and configured to rotate about a first pivot. A first actuator, configured on the user interface, is coupled with a first actuating portion first line that extends within and along the apparatus conduit to the first actuating portion. Utilizing a first manipulator, to pull and/or push on the first actuating portion first line rotates the first actuating portion about the first pivot. A first actuating portion second line may extend within and along the apparatus conduit from the user interface, such as from the first actuator to the first actuating portion and pushing and/or pulling of this second line may rotate the first actuating portion about the first pivot in an opposite direction from the direction of rotation caused by manipulation of the first actuating portion first line. For example, using the first manipulator and pulling on the first actuating portion first line may rotate the first actuating portion a first direction, such as clockwise, about the first pivot and pulling on the first actuating portion second line may rotate the first actuating portion a second direction, such as counter clockwise about the first pivot.

An exemplary intravascular articulating retrieval apparatus has a second actuating portion configured distal from the user interface and distal the first actuating portion and configured to rotate about a second pivot. A second actuator, configured on the user interface, is coupled with a second actuating portion first line that extends within and along the apparatus conduit to the second actuating portion. Pulling and/or pushing on the second actuating portion first line rotates the second actuating portion about the second pivot. A second actuating portion second line may extend within and along the apparatus conduit from the user interface, such as from the second actuator to the second actuating portion and pushing and/or pulling of this second line may rotate the second actuating portion about the second pivot in an opposite direction from the direction of rotation caused by manipulation of the second actuating portion first line. For example, pulling on the second actuating portion first line may rotate the second actuating portion a first direction, such as clockwise, about the second pivot and pulling on the second actuating portion second line may rotate the second actuating portion a second direction, such as counter clockwise about the second pivot.

In an exemplary embodiment, the axis of rotation of the first actuating portion about the first pivot and the axis of rotation of the second actuating portion about the second pivot may be parallel, wherein first and second actuating portions rotate in plane with each other. However, the second actuating portion may be configured to rotate at an offset angle with respect to the first actuating portion, such as orthogonally to the first actuating portion, wherein the axis of rotation of the first and second actuating portions about the first and second pivots, respectively, are orthogonal. Note that any other offset angle between the first and second actuating portions may be used as well.

An exemplary forceps has at least one jaw that is configured to open and close by manipulation of a retrieval actuator on the user interface. A retrieval line extends within and along the apparatus conduit to the forceps wherein manipulation of the retrieval actuator on the user interface pushes and/or pulls on the retrieval line to cause a first forceps jaw to open or close. In an exemplary embodiment, pushing on the retrieval line opens the first jaw and pulling on the retrieval line closes the first jaw against the second jaw. A first forceps jaw may rotate about a forceps pivot. A second jaw may be fixed and not rotate or may be configured to rotate about a forceps pivot, such as about a first jaw pivot or a separate, second jaw pivot. For example, a second retrieval line may extend from the retrieval actuator on the user interface within and along the apparatus conduit to the second jaw, or a jaw pivot and manipulation of the second retrieval line may open and close the second jaw. In an exemplary embodiment, the first and second jaws rotate about a single jaw pivot, wherein pushing or pulling of a single retrieval line opens and closes both the first and second jaws, which both rotate about said single jaw pivot.

An exemplary jaw may have a serrated edge to provide better gripping of tissue or a device, such as an IVF. The serrations may have backward facing teeth, or teeth that face the user interface end to better retain object therein. In an exemplary embodiment, both jaws have serrated edges and the jaws may be alligator jaws. In another embodiment, the jaws are tweezer jaws having elongated curved jaws that interface only on the extended ends, wherein the extended jaw ends come together when the jaws are closes or wherein the extend past each other when the jaws or closes. An exemplary tweezer jaws may enable both the extend ends of the first and second jaw to extend through an aperture of a device to better secure the device for retrieval, especially when the extended ends are configured to extend past each other when closed. An exemplary forceps may have a cutting jaw having a blade edge or sharp edge for cutting of tissue or a device, such as a graft. In an exemplary embodiment, a forceps has scissor jaws, having at least one of the first or second jaws having a blade edge and wherein the first and second jaws are configured to extend over each other, or overlap to enable scissor cutting. A forceps may form a retainer aperture between the two jaws when closed, thereby enabling capture of a device or part of a device within the retainer aperture. An exemplary forceps may have an retainer aperture configured between the first and second jaws to create an opening for retaining an object therein.

An exemplary retrieval implement may be an expandable funnel sheath that can be opened and contracted around an object for retrieval or movement within the vasculature. An exemplary expandable funnel sheath may have an extended end that forms an opening and the sheath may taper from the extended end to the coupled end, the end coupled with the distal end of the catheter.

An exemplary retrieval implement may be a hook that can be turned and manipulated by the actuating portion or portions. The hook portion of the hook, may be used to snare an object in the body for retrieval or movement. An object may be retained within the slot or opening formed between the hook portion and the hook arm. An exemplary hook may be a coil hook, or a hook that can be manipulated to coil and form a closed hook in-situ. A closed hook may have the extended end pulled down to the hook arm to form a hook aperture. A retrieval line may be coupled proximal to the extended end of a hook portion and pulling on the retrieval line may cause the extended end to coil back over the hook arm to form a coil hook. In an exemplary embodiment, a pair of coil hooks are configured as a retrieval implement. Each of the pair of coil hooks may be manipulated to form a coil hoop, or opening between the two coil hooks for retaining an object.

An exemplary apparatus conduit and/or the forceps attached thereto, may be small in dimension to enable maneuvering through small vessels and may have a diameter, or be configured to extend through a vessel wall having an interior diameter of no more than about 20 French, or preferably no more than 18 French, or no more than 10 French or about 6 French or more and any range between and including the diameters provided.

An exemplary apparatus conduit may be made out of a flexible material to enable maneuvering through the vascular or gastro intestinal system and may be made out of metal, or plastic.

The user interface may include a first actuator for the first actuating portion, a second actuator for the second actuator portion and a retrieval actuator for actuating the retrieval implement, such as at least one of the jaws of the forceps. An exemplary actuator may be a paddle, wherein rotation of the paddle a first rotational direction pulls on the line extending therefrom and rotation of the paddle a second rotation direction pushes on the line extending therefrom. An exemplary actuator may be a dial, wherein rotation of the dial a first rotational direction pulls on the line extending therefrom and rotation of the dial a second rotation direction pushes on the line extending therefrom. An exemplary actuator may be a handle, wherein pulling on the handle pulls the line and pushing on the handle pushes the line extending therefrom.

An exemplary intravascular articulating retrieval apparatus may be used in any number of intravascular procedures including, but not limited to, retrieval of an IVF, blunt dissection of tissue including plaque and/or thrombus. An exemplary intravascular articulating retrieval apparatus may be retrofitted with a scope, or camera, and may be used for investigation an imaging of the vascular and/or organs including the heart, lungs, gastrointestinal and the like. The exemplary intravascular articulating retrieval apparatus may be used for the removal of a piece of tissue as often necessary in humans and animals to make a diagnosis of cancer or to remove a purposefully or accidentally placed foreign body into the vascular system.

An exemplary intravascular articulating retrieval apparatus may be used to remove IVF's under fluoroscopic guidance, and with the ability to be redirected in three dimensions within a large vessel through percutaneous access. The device shaft may be a malleable metal, and capable not only of providing tensile force, but also a fair amount of compressive force so as to be able to direct the forceps appropriately. An exemplary intravascular articulating retrieval apparatus may also be flexible enough to navigate extensive vascular curvature. Exemplary forceps jaws are shaped to be able not only to grasp the device anywhere along the body (not just the intended hook), but will also be able to bluntly dissect overgrown tissue along the filter to better allow removal of a remotely placed filter.

An exemplary intravascular articulating retrieval apparatus is likely to be the only tool necessary to remove many foreign bodies from the inferior vena cava, but specifically any and all inferior vena cava filters, whether designed to be retrievable or not, and across all different company platforms. An exemplary intravascular articulating retrieval apparatus will change the way inferior vena cava filters are designed, and the idea that they may not be removed after a certain amount of time within the body. Additional, smaller iterations of an exemplary intravascular articulating retrieval apparatus may be used in the future to retrieve intravascular foreign bodies in the heart, lungs, neck, extremities, and brain.

The method of use of an exemplary externally mechanically controlled actuating manipulator encompasses any endovascular device that is controlled by a relatively large mechanical actuator outside the body. In general, this actuator articulates the apparatus to allow precise access to 360 degrees of the inner lumen of the vasculature. Furthermore, this device generally works through a sheath or a catheter, and therefore has a relatively slim profile when compared with the actuator. Advantages of a relatively large actuator that allows articulation include more precise manipulation, precise access to any part of the vessel lumen, as well as the use of increased manual force. Up to this point, the vast majority of intravascular devices utilize wires and catheters only, allowing only minimal force to be translated, and access only to the portion of the vessel directly in line with the tip of the catheter. The catheter can be rotated, but many times the tortuosity of the vasculature limits 1:1 rotation of the catheter, and precise manipulation is not possible. Additionally, the diameter of the vessel lumen sometimes prohibits access to portions of the vessel wall with a straight or minimally curved flexible catheter.

There are also many other intravascular applications such as cutting, remodeling, ablating, biopsy performance, tissue removal, and intravascular ultrasound which would also benefit from an intravascular articulating apparatus that is a mechanical externally directed intravascular manipulator as described herein. A camera, ablation tool, or other device may be configured in place of the retrieval implement.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 19 shows a cross-sectional view of an exemplary articulating retrieval apparatus and a first actuator having a first manipulator.

FIG. 20 shows a cross-sectional view of the exemplary articulating retrieval apparatus shown in FIG. 19 with the manipulator manipulated to actuate the first actuating portion.

FIG. 21 shows a cross-sectional view of an exemplary articulating retrieval apparatus and a user interface having a first and second actuator and first and second manipulators for actuating the first and second actuating portions.

FIG. 22 shows a cross-sectional view of the exemplary articulating retrieval apparatus shown in FIG. 21 with the first manipulator manipulated to actuate the first actuating portion.

FIGS. 29 to 31 show an exemplary articulating retrieval apparatus retrieving an intravascular filter from a vascular wall.

FIGS. 32 to 34 show an exemplary articulating retrieval apparatus retrieving an intravascular filter from a vascular wall utilizing an inflatable balloon.

FIG. 43 shows a top view of an exemplary actuating forceps apparatus.

FIG. 44 shows a right side view of an exemplary actuating forceps apparatus.

FIG. 45 shows a front view of an exemplary actuating forceps apparatus.

Figure 1:
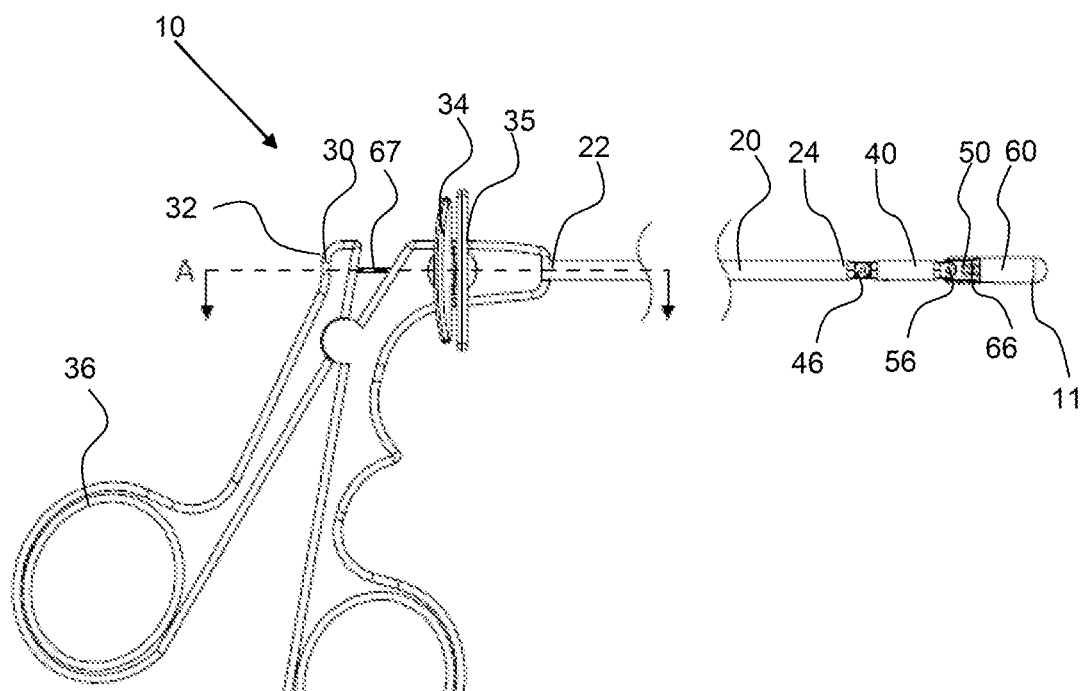
FIG. 1 shows a side view of an exemplary actuating retrieval apparatus having a user interface and a forceps end having forceps having a first and second jaw.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE
ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 2:
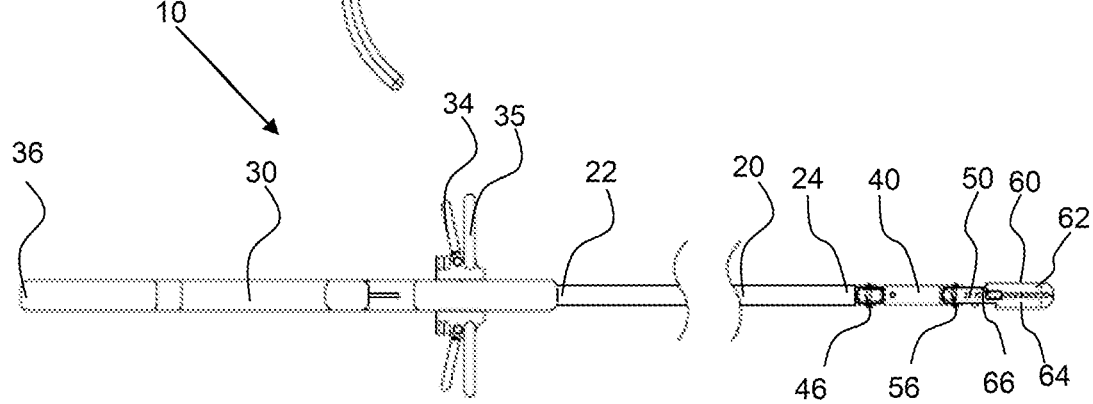
FIG. 2 shows a top view of the exemplary articulating retrieval apparatus shown in FIG. 1.
Figure 3:
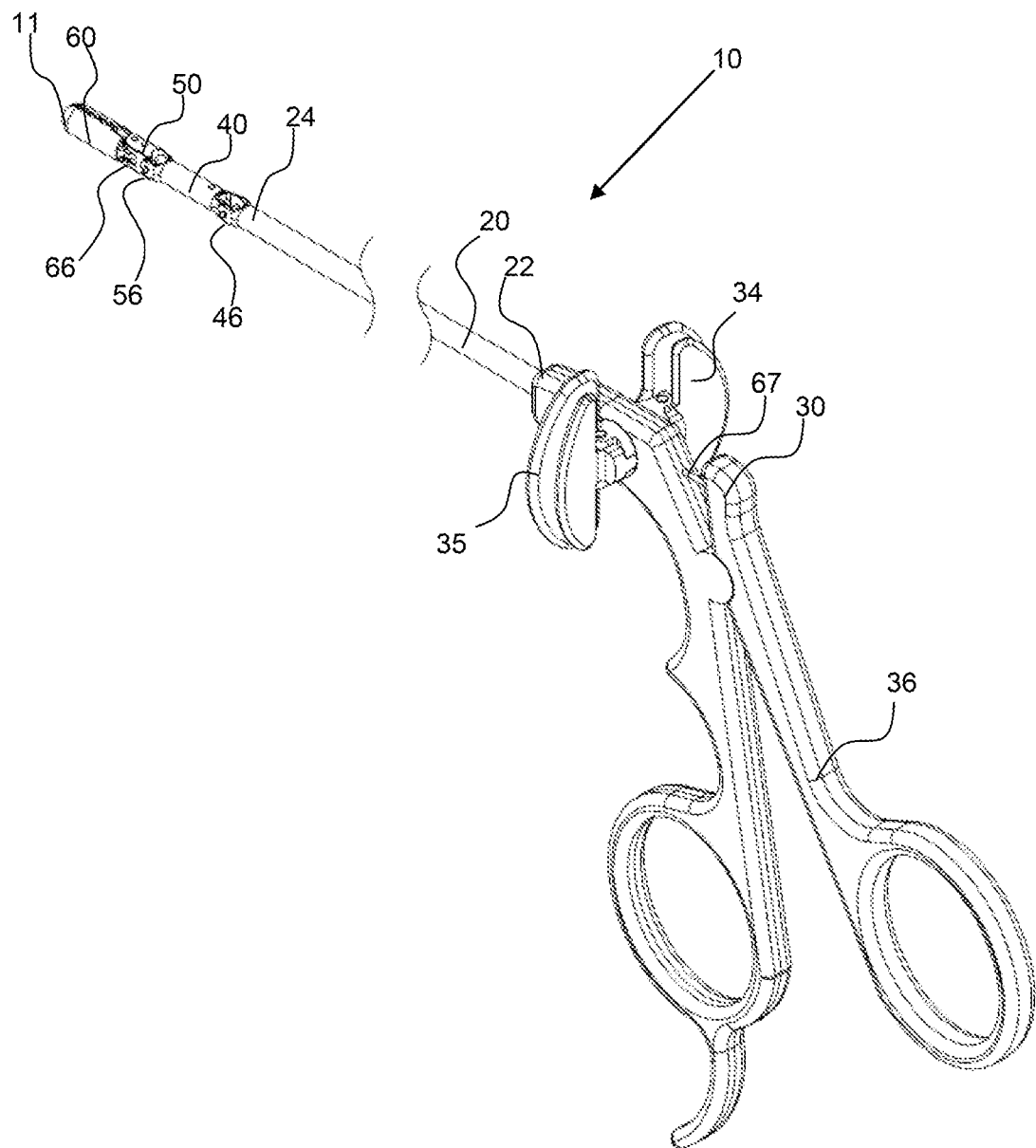
FIG. 3 shows a perspective view of the exemplary articulating retrieval apparatus shown in FIG. 1.

Referring now to FIGS. 1 to 3, an exemplary articulating retrieval apparatus 10 has a user interface 30 and a forceps end having forceps 60 comprising a first and second jaw. An apparatus conduit 20 extends a length from the user interface end or user end 22 to the distal end 24 wherein a first actuator 40 is coupled thereto. The first actuator is configured to rotate about a first pivot 46 and extends from a coupled end to a distal end. A second actuator 50 is coupled to the first actuator and is configured to rotate about second pivot 56 and extends from a coupled end to a distal end. The forceps are coupled to the second actuator. The actuating assembly 14 has two degrees of freedom. Actuating lines extend from the actuating portions down the apparatus conduit to the user interface. On the user interface end 32 a user may utilize a first actuator 34 to actuate the first actuating portion 40 and a second actuator 35 to actuate the second actuating portion 50. A first jaw of a forceps may be opened and closed using a retrieval actuator 36 that is coupled with a first retrieval line 67 that also extend through the apparatus conduit to the forceps 60. The first jaw rotates about the jaw pivot 66.

Figure 4:
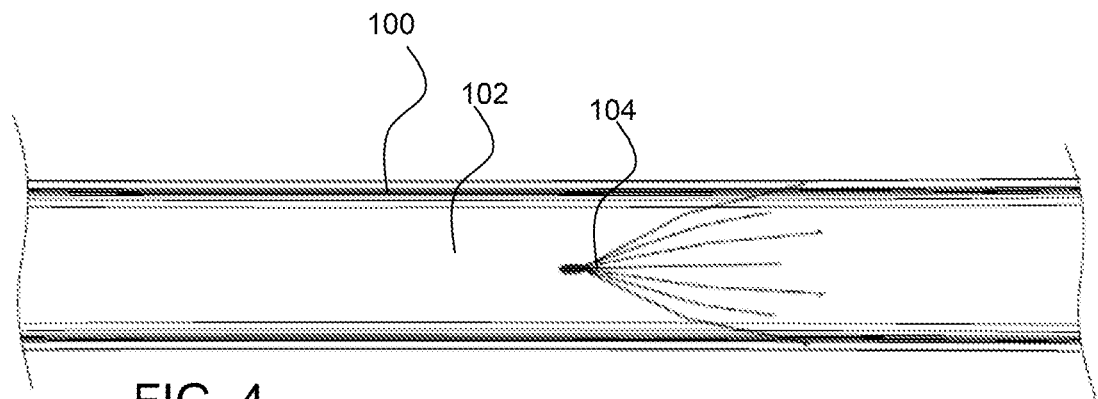
FIGS. 4 to 6 show a vascular wall having an intravascular filter therein.
Figure 5:
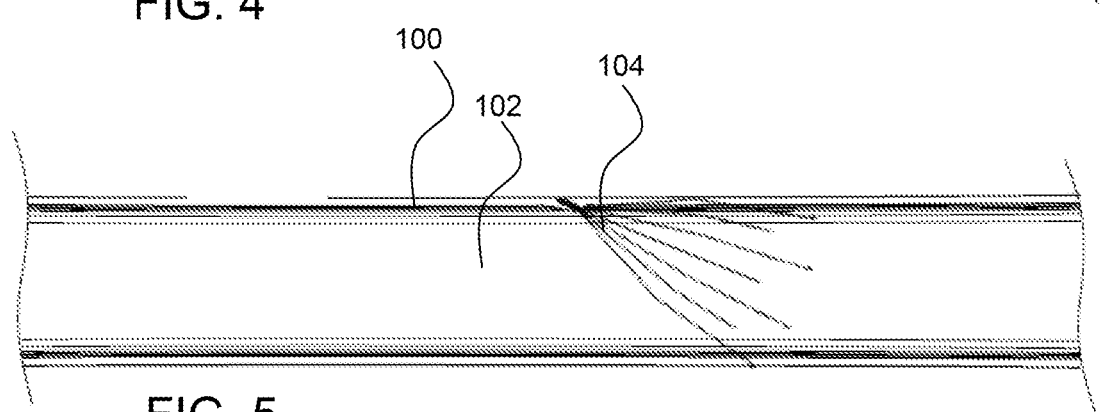
Figure 6:
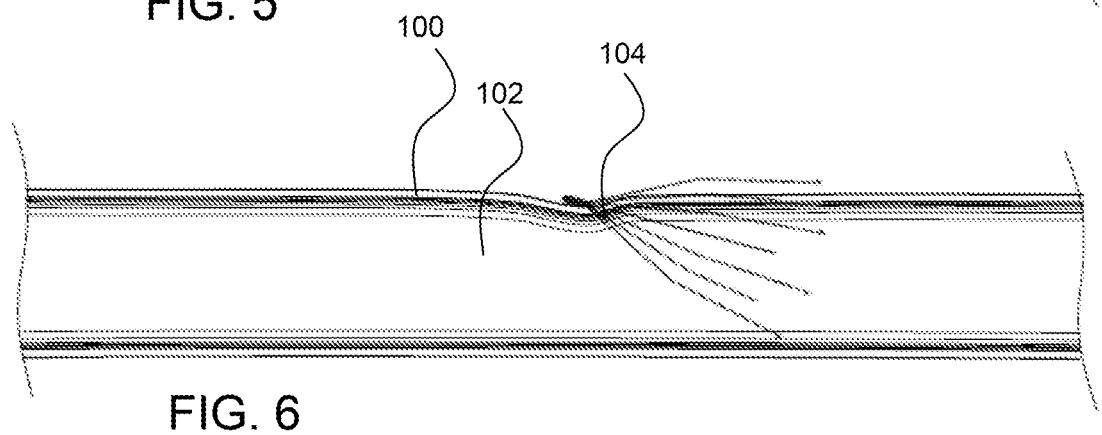

FIGS. 4 to 6 show a vascular wall 100 having an intravascular filter (IVF) 104 therein. In FIG. 4 the IVF is within the vascular conduit 102. In FIG. 5, the IVF is lodged in the vascular wall. In FIG. 6, the IVF filter has penetrated through the vascular wall.

Figure 7:
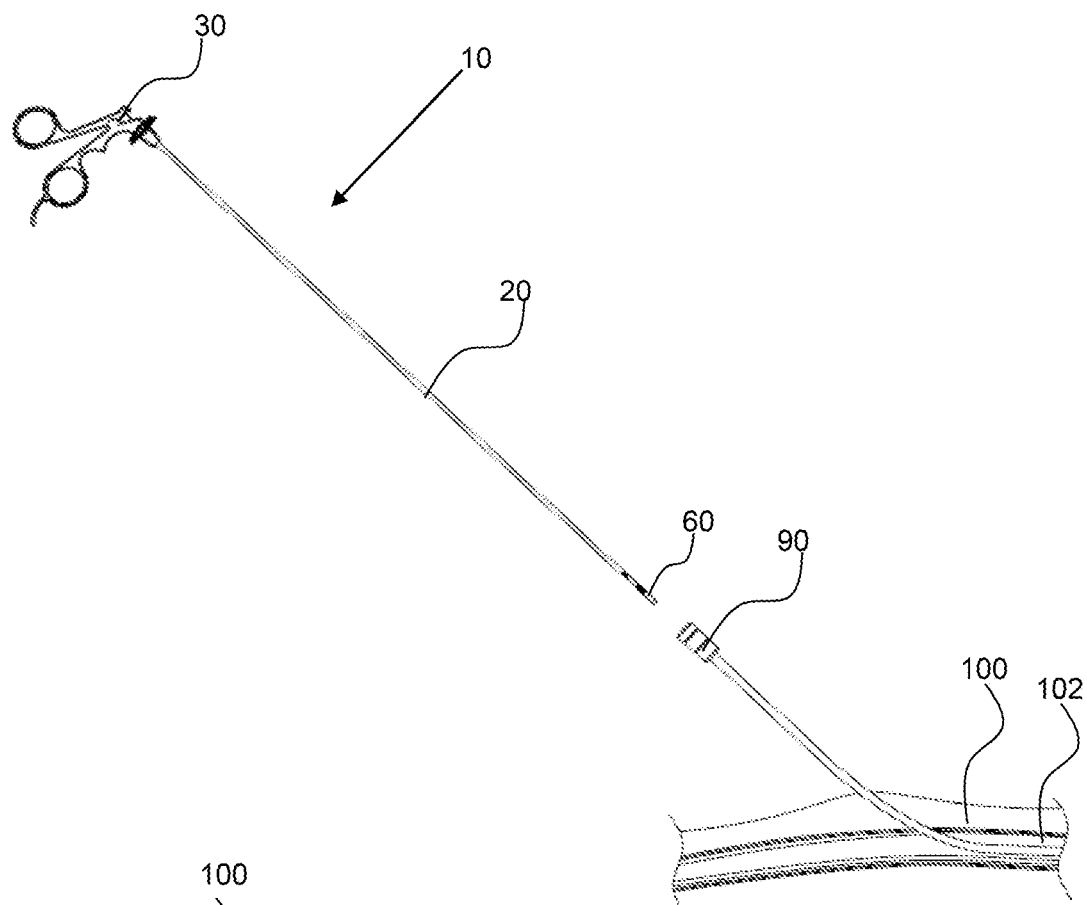
FIG. 7 shows an introducer sheath and an exemplary articulating retrieval apparatus configured to extend into a vascular vessel through the introducer sheath.
Figure 8:
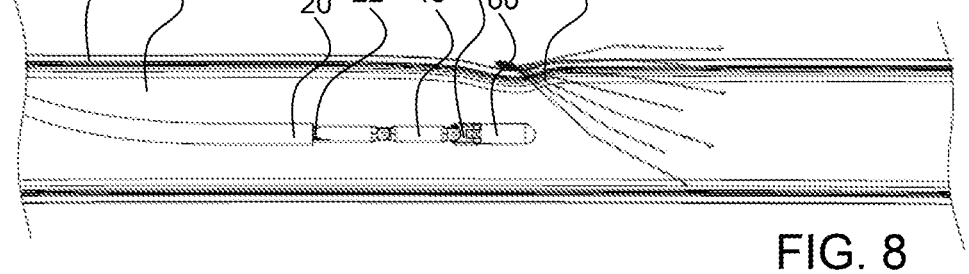
FIGS. 8 and 9 show an exemplary articulating retrieval apparatus configured in a vascular vessel and being actuated to retrieve an intravascular filter lodged in the vascular wall.
Figure 9:
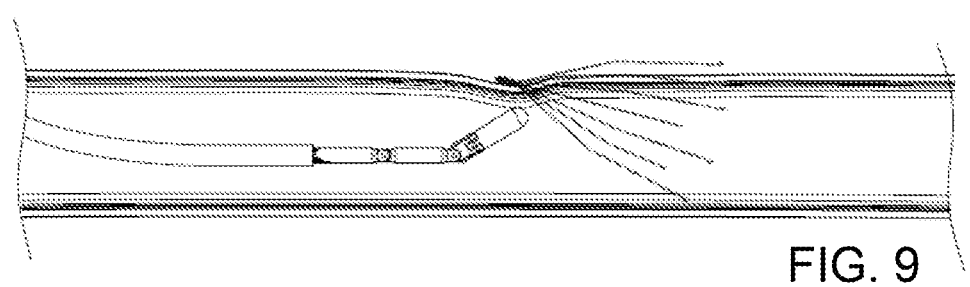

Referring now to FIGS. 7 to 9, an introducer sheath 90 is configured through a vascular wall 100 and an exemplary articulating retrieval apparatus 10 is configured to extend into a vascular vessel through the introducer sheath. As shown in FIG. 8, the exemplary articulating retrieval apparatus is configured within the vascular wall. As shown in FIG. 9 the exemplary articulating retrieval apparatus is being actuated to locate the forceps proximal to the IVF for retrieval of the IVF.

Figure 10:
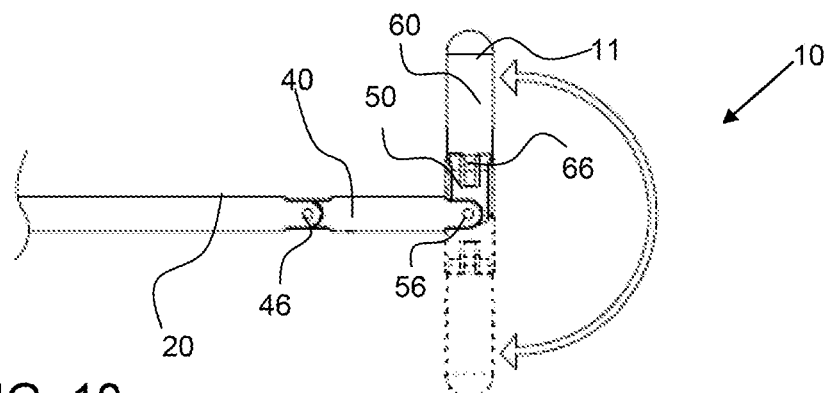
FIG. 10 shows a side view of an exemplary articulating retrieval apparatus having the second actuating portion actuated orthogonally to the length axis of the apparatus conduit.
Figure 11:
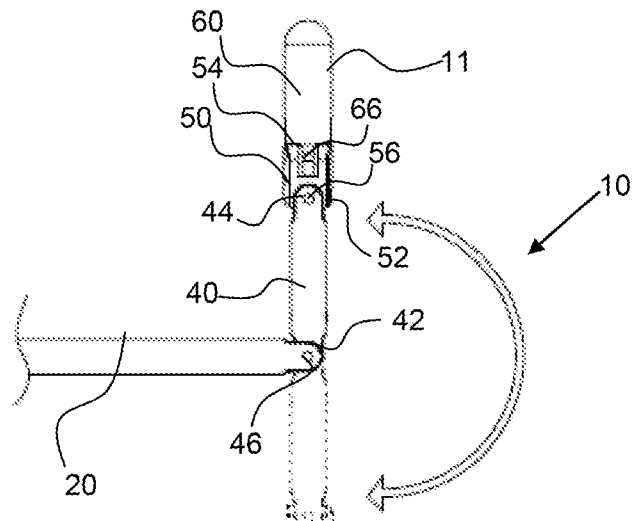
FIG. 11 shows a side view of an exemplary articulating retrieval apparatus having the first actuating portion actuated orthogonally to the length axis of the apparatus conduit.
Figure 12:
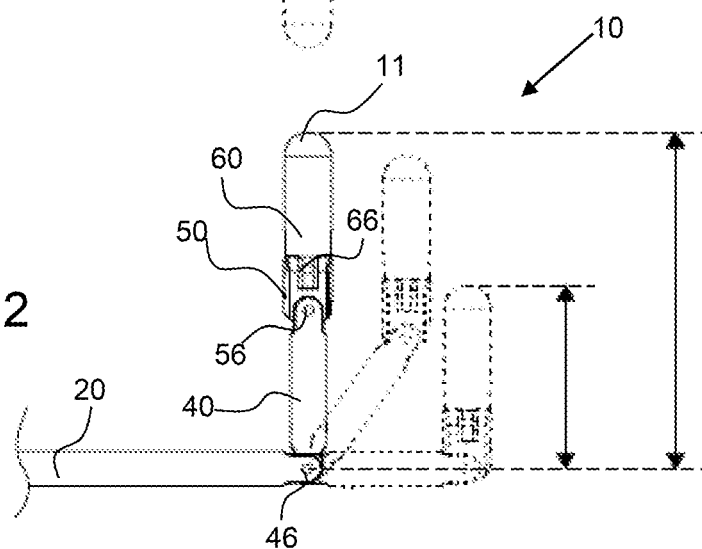
FIG. 12 shows a side view of an exemplary articulating retrieval apparatus having the second actuating portion actuated orthogonally to the length axis of the apparatus conduit.

Referring now to FIGS. 10 to 12, an exemplary articulating retrieval apparatus 10 has a first actuating 40 and a second actuating portion 50 that can be actuated separately. As shown in FIG. 10, the second actuating portion 50 is actuated orthogonally to the length axis of the apparatus conduit 20. The first actuator is configured to rotate about a first pivot 46 and extends from a coupled end 42 to a distal end 44. The second actuator 50 is coupled to the first actuator about the second pivot 56 and is configured to rotate about second pivot 56 and extends from a coupled end 52 to a distal end 54. As shown in FIG. 11, the first actuating portion 40 is actuated orthogonally to the length axis of the apparatus conduit 20. FIG. 12 shows the actuation of the first actuating portion from parallel with the length axis of the apparatus conduit to orthogonal to the length axis of the apparatus conduit. The length of the first or second actuating portion from the coupled end to the distal end may be about 15 mm or less, about 10 mm or less, about 5 mm or less, about 3 mm or less, about 2 mm or less and any range between and including the values provided.

Figures 13, 14:
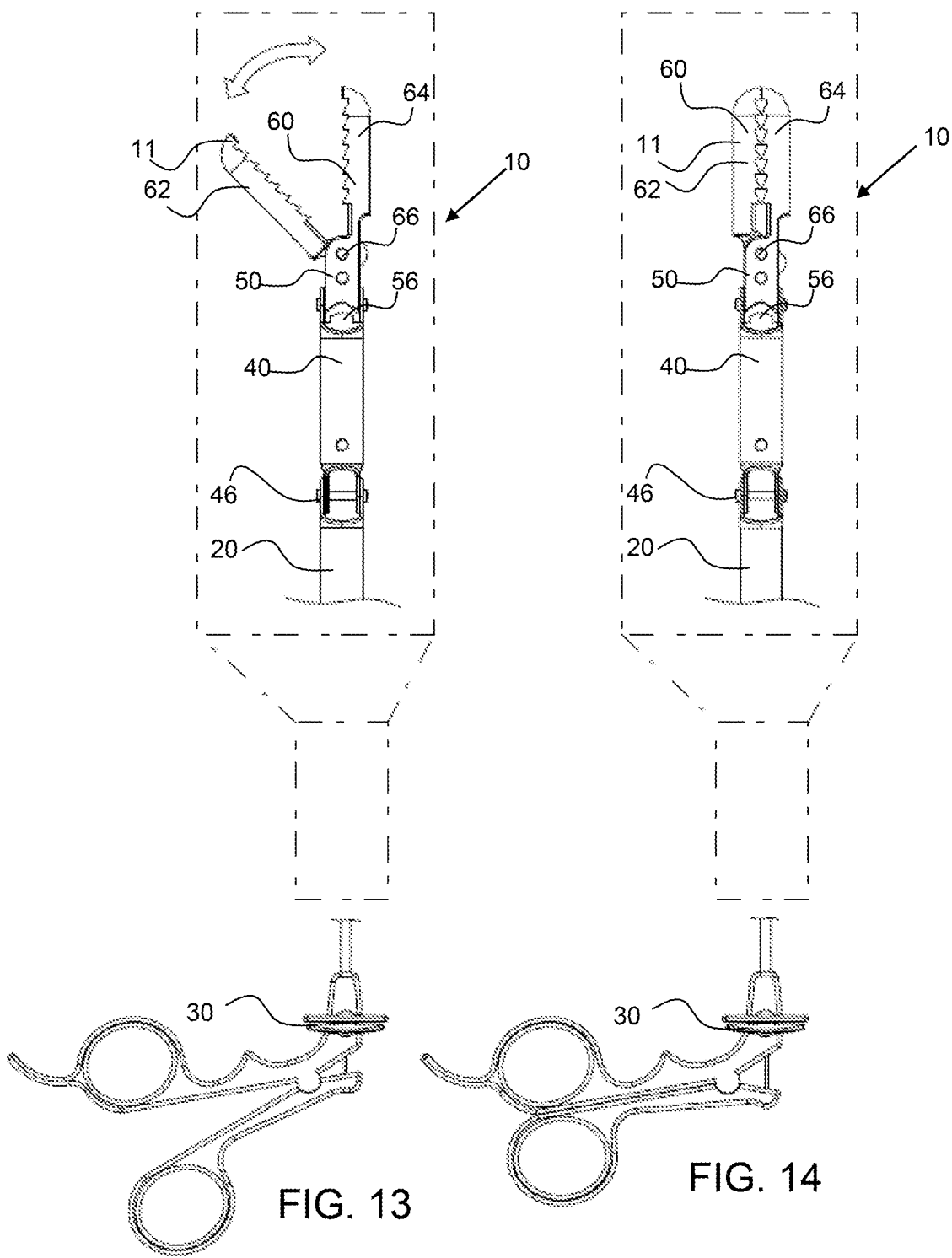
FIG. 13 shows a side view of an exemplary articulating retrieval apparatus having the first jaw open.
FIG. 14 shows a side view of an exemplary articulating retrieval apparatus having the first jaw closed.
Figure 15:
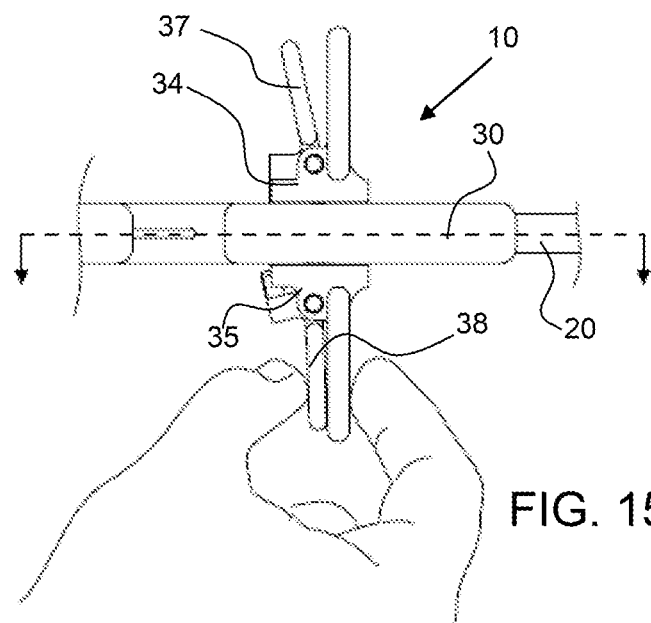
FIG. 15 shows a top view of a user interface of the exemplary articulating retrieval apparatus having a first actuator and first manipulator and a second actuator and second manipulator.

Referring now to FIGS. 13 and 14, an exemplary articulating retrieval apparatus 10 has forceps 60 with a first actuating jaw 62 and a second jaw 64. As shown in FIG. 13, the first jaw is in an open orientation and in FIG. 14, the first jaw is in a closed orientation. The first jaw rotates about jaw pivot 66.

Figure 16:
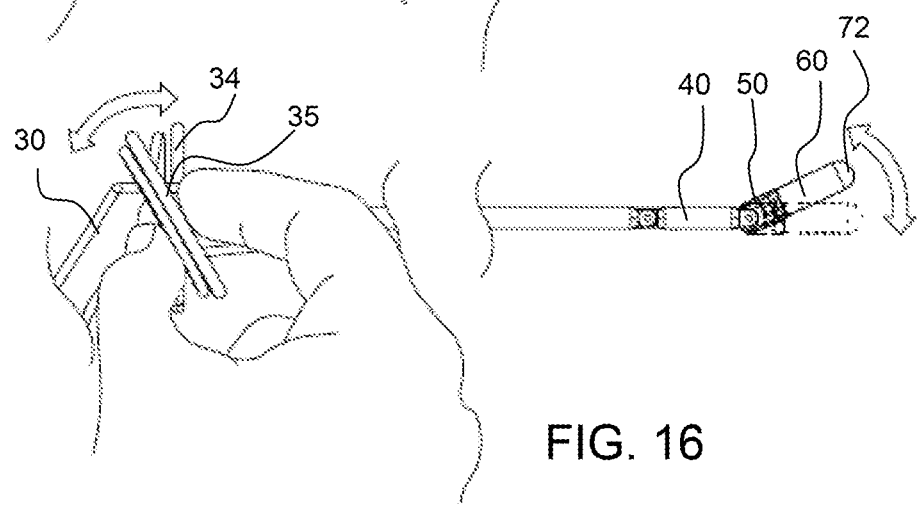
FIG. 16 shows a side view of an exemplary articulating retrieval apparatus having the second manipulator rotated to actuate the second actuating portion and the forceps coupled thereto.
Figure 17:
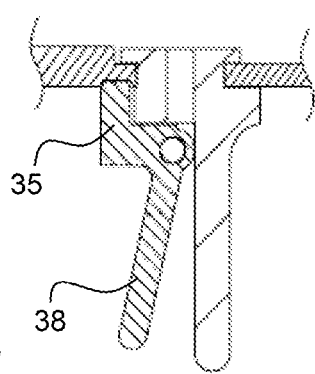
FIGS. 17 and 18 show a cross-sectional view of an exemplary actuator having a manipulator.
Figure 18:
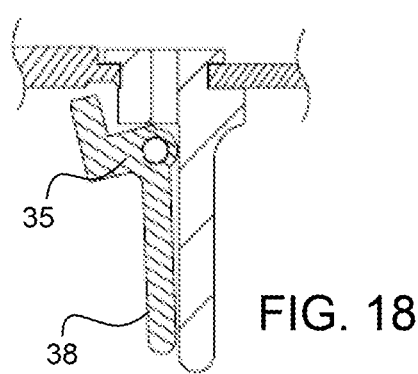

Referring now to FIGS. 15 to 18, an exemplary articulating retrieval apparatus 10 has a user interface 30 having a first actuator 34 and a second actuator 35. The first actuator has a second manipulator 38, a paddle, that the user is rotating to actuate the second actuating portion 50, as shown in FIG. 16. The user interface also has a first manipulator 34, for actuating the first actuating portion. At least one of the jaws of the forceps 60 may be configured with a blade or blade edge 72 to enable cutting of a device or biological tissue along the vasculature.

As shown in FIGS. 19 and 20, an exemplary articulating retrieval apparatus 10 has a first actuator 34 having a first manipulator 37. The first actuator is coupled with the first actuating portion first line 47 and first actuating portion second line 48. Rotation of the first manipulator a first direction pulls on the first actuating portion first line 47 as shown in FIG. 20 and conversely, rotation of the first manipulator a second direction opposite the first direction, pulls on the first actuating portion second line 48 to actuate the first actuating portion an opposite direction about the first pivot 46.

Referring now to FIGS. 21 and 22, an exemplary articulating retrieval apparatus 10 has a first actuator 34 having a first manipulator 37 and a second actuator 35 having a second manipulator 38. The first and second manipulators are dial that rotate a worm gear 33 coupled with an actuating gear. Rotating the dial in a first direction pulls on the first actuating portion first line 47 as shown in FIG. 22 to rotate the first actuating portion a first direction about the first pivot 46.

Figure 23:
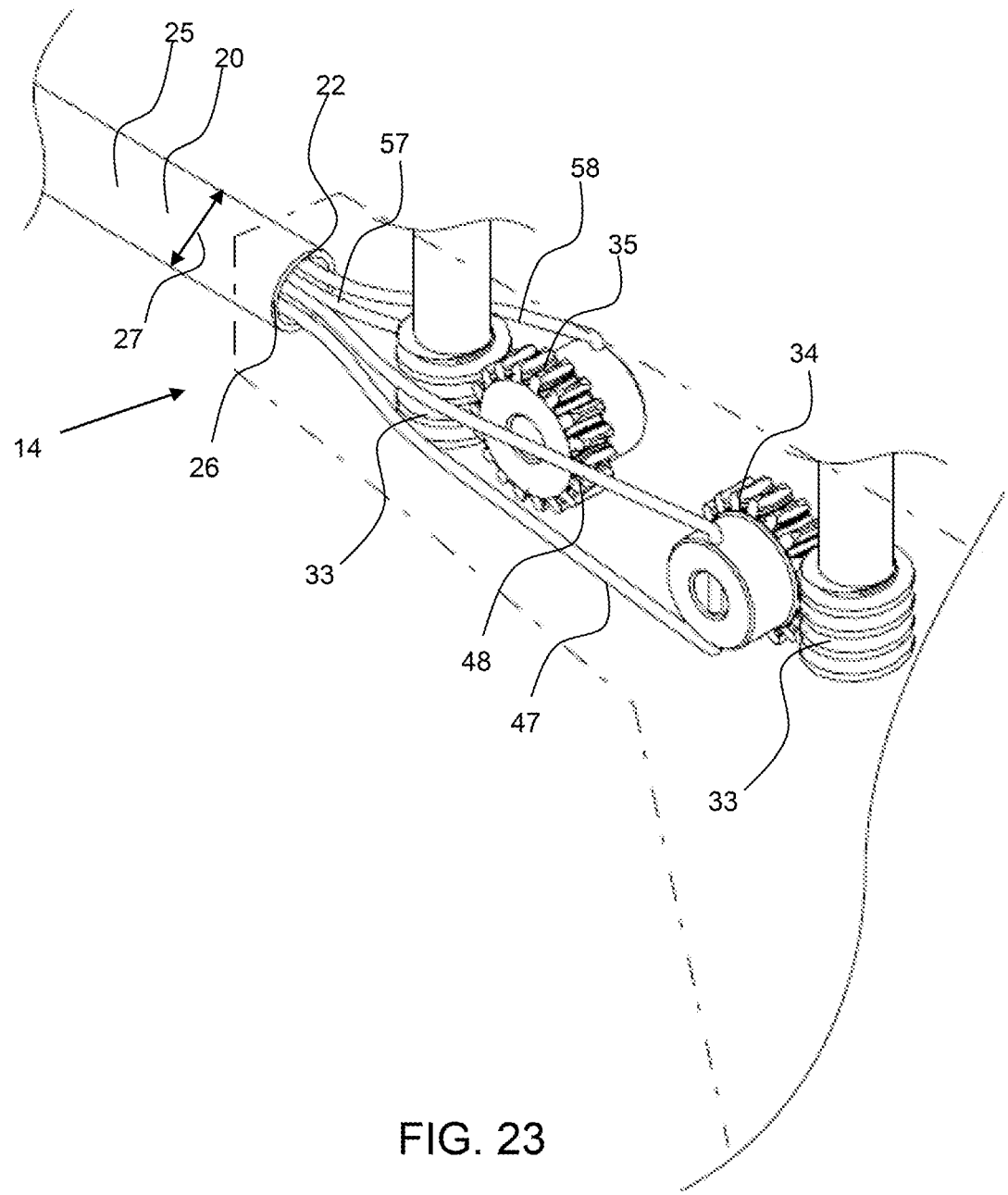
FIG. 23 shows cut away view of a user interface having a first and second actuator and first and second manipulators for actuating the first and second actuating portions.

FIG. 23 shows cut away view of a user interface 30 having a first actuator 34 and second actuator 35 and first and second manipulators for actuating the first and second actuating portions. The first actuator 34 is coupled with the first actuating portion first line 47 and first actuating portion second line 48. A worm gear 33' is configured between the first actuator and the first manipulator. The second actuator 35 is coupled with the second actuating portion first line 57 and second actuating portion second line 58. A worm gear 33 is configured between the second actuator and the second manipulator. This actuating assembly 14 enables controlled actuation of the first and second actuating portions separately. This exemplary actuator comprises a worm gear assembly. The actuating lines extend into the conduit 26 of the apparatus conduit 20 having a conduit wall 25 and an outer diameter 27 and inner diameter.

Figures 24, 25:
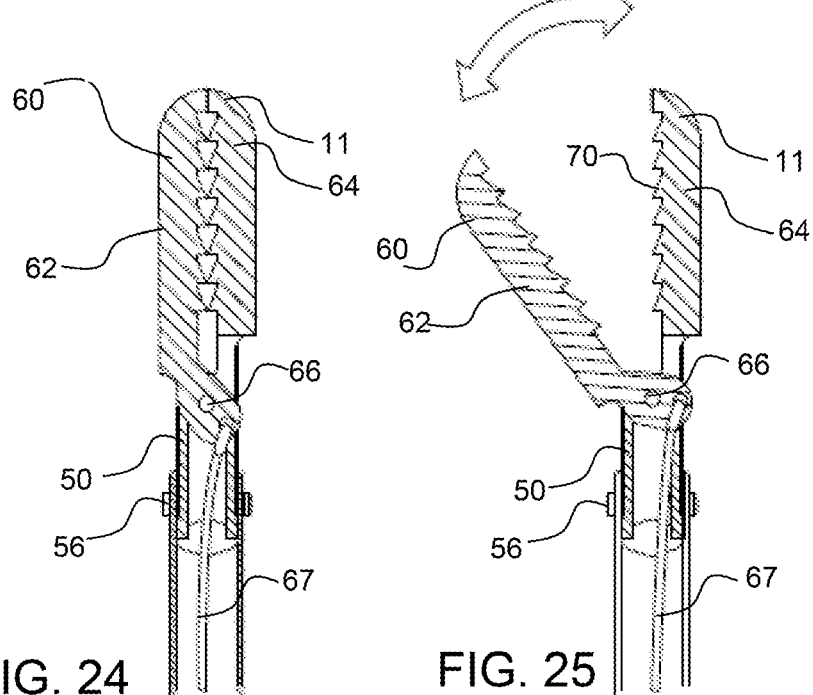
FIGS. 24 and 25 show exemplary forceps having a first and second jaw.

FIGS. 24 and 25 show exemplary forceps 60 having a first actuating jaw 62 and second jaw 64. The first jaw is coupled with the first retrieval line 67 and pivots about jaw pivot 66. Both jaws have a serrated edge 70 to provide better gripping. The serrations form backward facing teeth to retain an object, such as an intravascular filter or tissue. A user interface, not shown pulls and pushes on the retrieval line to close and open the first jaw, respectively.

Figures 26, 27, 28:
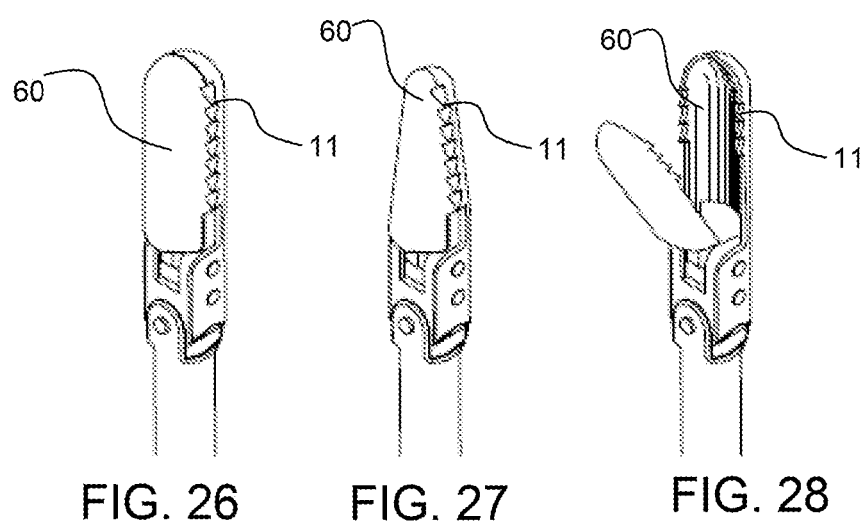
FIGS. 26 to 28 show exemplary forceps having a first and second jaw.

FIGS. 26 to 28 show exemplary forceps having a first and second jaw. As shown in FIG. 26 the jaws are alligator jaws, having a rounded end with serrations. As shown in FIG. 27, the jaws are alligator jaws that have a smaller radius end.

FIGS. 29 to 31 show an exemplary articulating retrieval apparatus retrieving an intravascular filter from a vascular wall.

FIGS. 32 to 34 show an exemplary articulating retrieval apparatus retrieving an intravascular filter from a vascular wall utilizing an inflatable balloon 80 that is coupled to a balloon line. The balloon line is a conduit to enable gas to fill and inflate the balloon.

Figure 35:
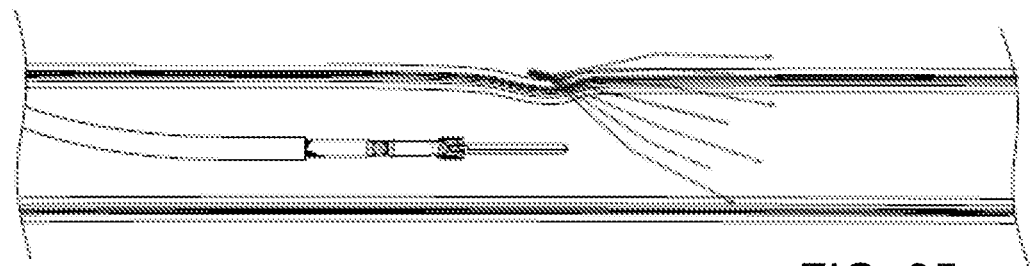
FIGS. 35 and 36 show an exemplary articulating retrieval apparatus retrieving an intravascular filter from a vascular wall.
Figure 36:
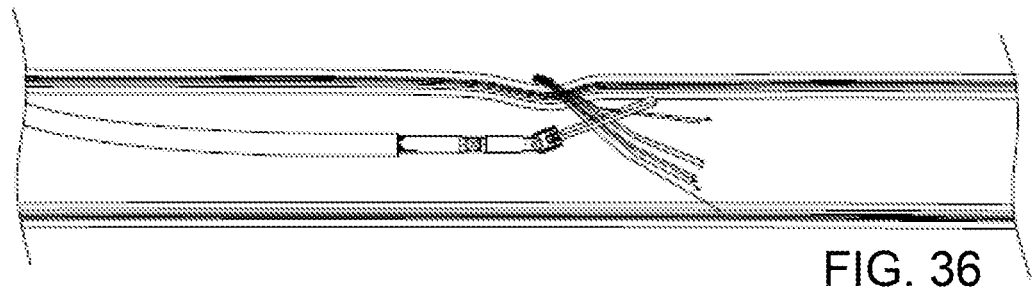

FIGS. 35 and 36 show an exemplary articulating retrieval apparatus retrieving an intravascular filter from a vascular wall.

Figures 37, 38, 39:
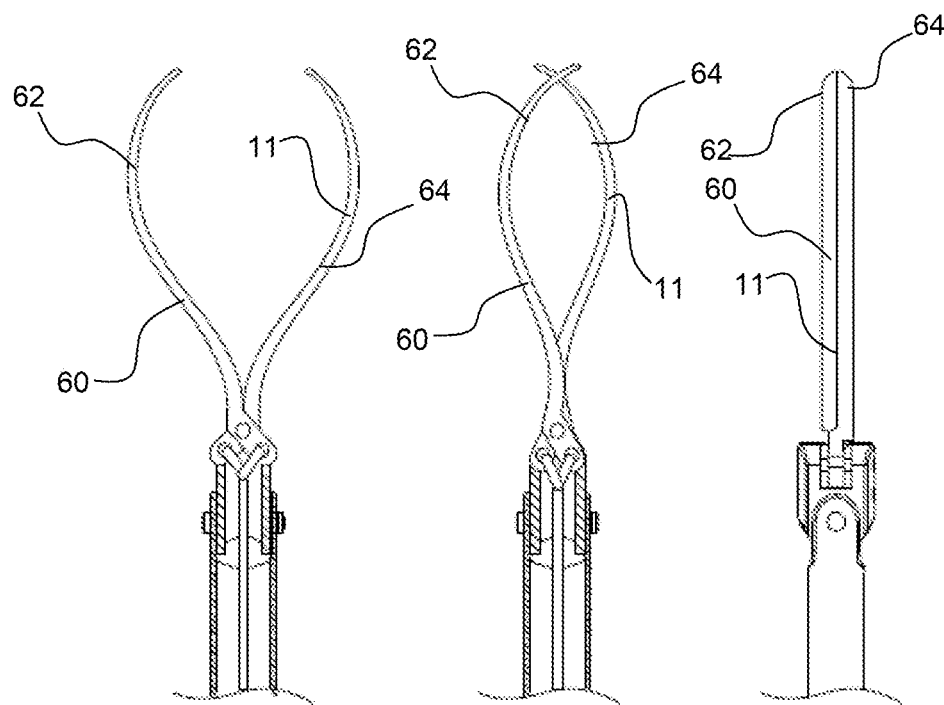
FIGS. 37 to 39 show various forceps structures having a first and second jaw.
Figure 40:
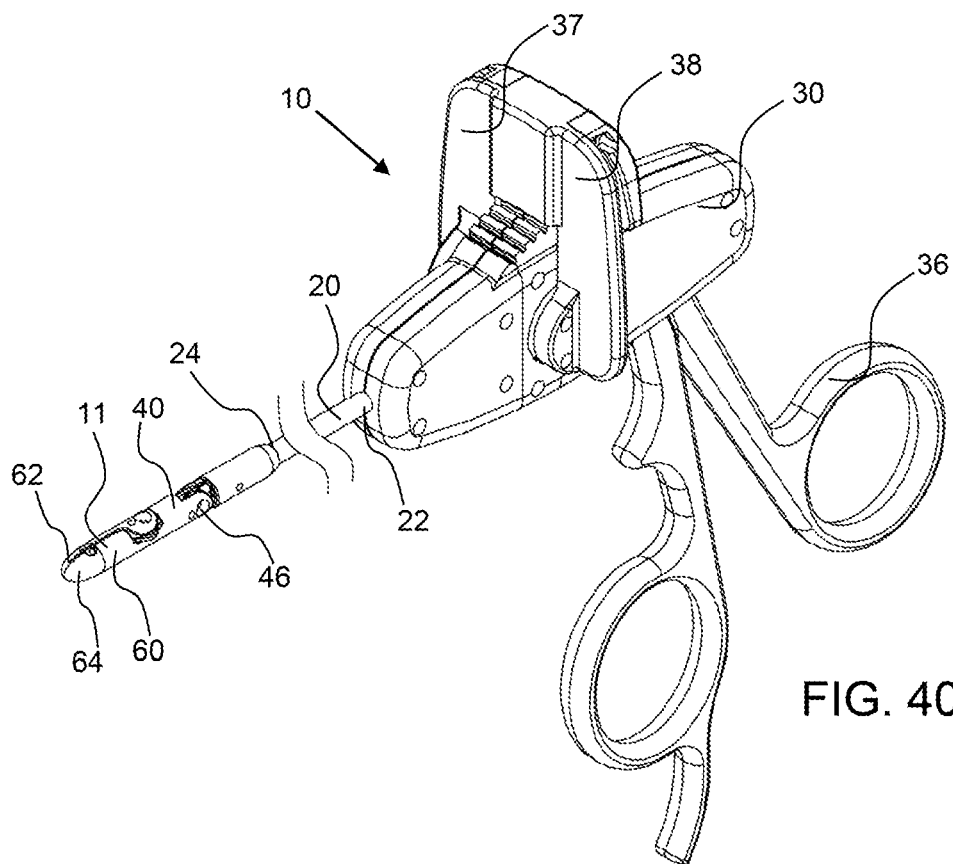
FIG. 40 shows a perspective view of an exemplary actuating forceps apparatus.

FIGS. 37 to 39 show various forceps 60 having a first actuating jaw 62 and second jaw 64. As shown in FIG. 37, the jaws are tweezer jaws having pointed ends. As shown in FIG. 38 the tweezer jaws are configured to overlap at the extended ends, which may aid in retaining an object therein. FIG. 39 shows the two tweezer jaws configured parallel to each other to allow the extended ends to overlap, as shown in FIG. 38.

Referring now to FIGS. 40 to 48, an exemplary articulating retrieval apparatus 10 has forceps 60, one type of a retrieval implement 11, configured on the distal end 24 of a catheter 20. The catheter is coupled on the user interface 30, on the user end of the catheter. The user implement enables a user to open and close one or both of the forceps jaws. The retrieval actuator 36 is configured as a handle to enable opening and closing of the first actuating jaw 62 with respect to the second jaw 64. The forceps is configured on a first actuating portion 40, that is configured to rotated about the first pivot 46. The actuating portion or portions may be controlled by the first manipulator 37 and second actuator 38; shown as paddle extending from the top of the user interface 30. The retrieval implement shown is coupled to a single actuating portion but a second actuating portion may be use to increase the degrees of freedom of motion. Note that the retrieval implement 11 may be detachably attachable to an actuating member thereby enabling interchanging of the type of retrieval implement used with the user interface 30. The user interface may still be used to articulate the retrieval implement and the retrieval actuator 36 or implement actuator, may be used to open and close a jaw or manipulate the retrieval implement in some way to hold a foreign article, such as an IVC filter, for removal from the body.

Figure 41:
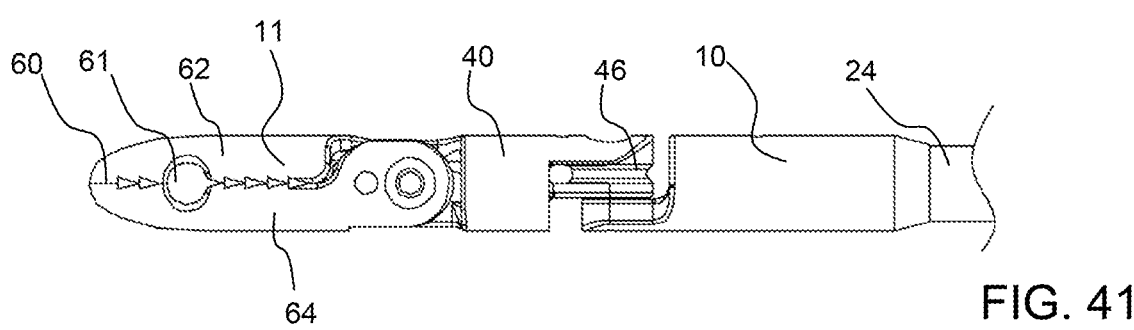
FIG. 41 shows a top view of exemplary articulating forceps having a retainer aperture between the jaws.
Figure 42:
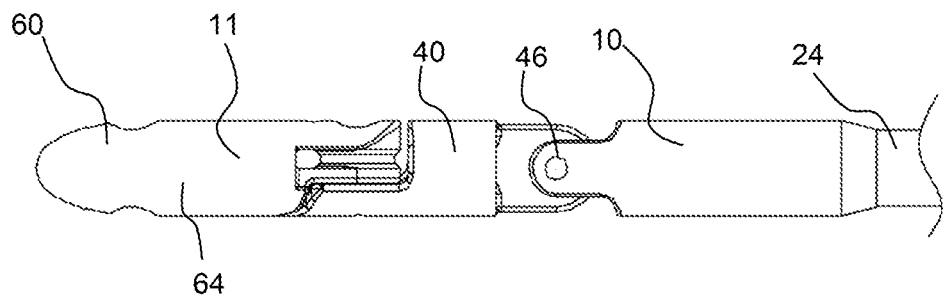
FIG. 42 shows a side view of the exemplary articulating forceps shown in FIG. 41.
Figures 46, 47:
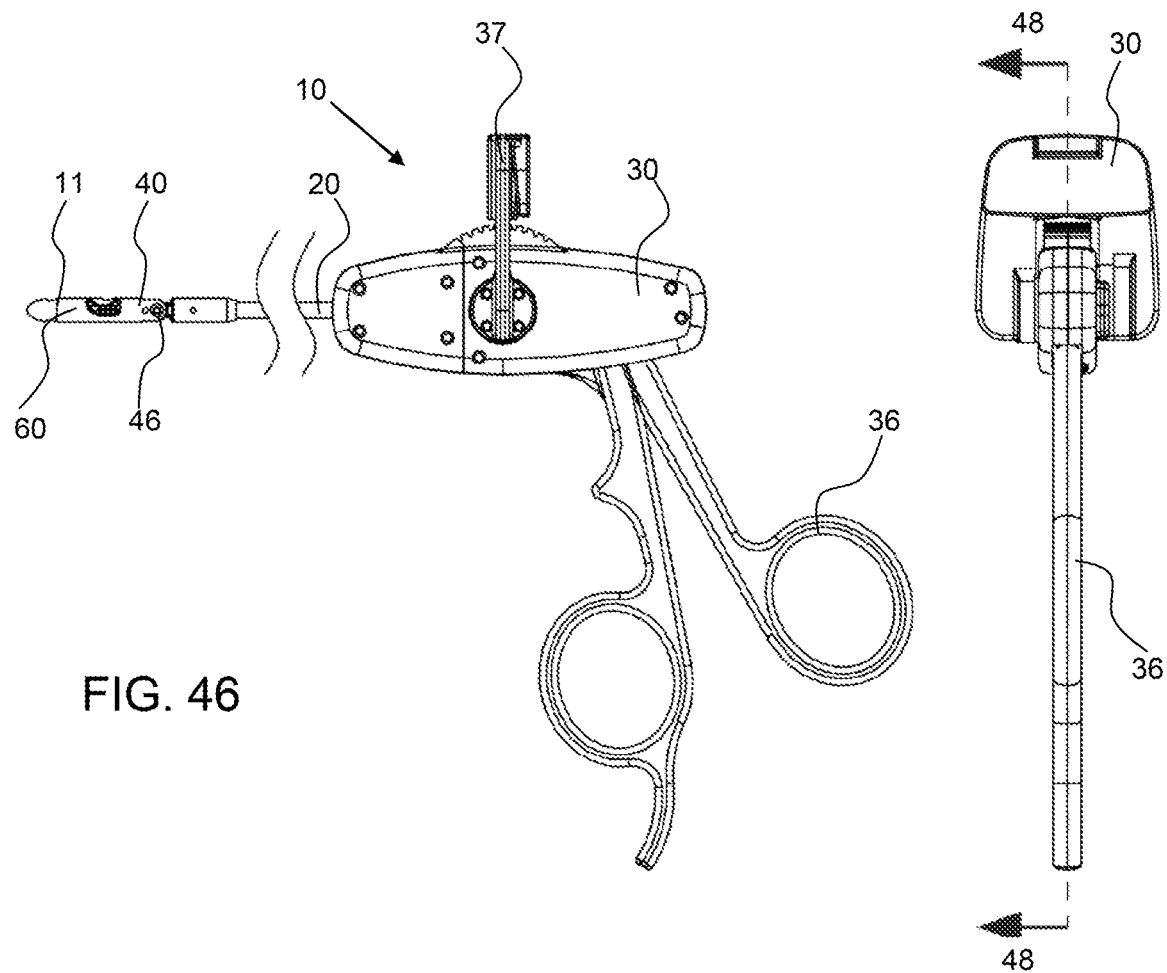
FIG. 46 shows a left side view of an exemplary actuating forceps apparatus.
FIG. 47 shows a back view of an exemplary actuating forceps apparatus.

As shown in FIGS. 41 and 42, the retrieval implement 11, forceps, have a retainer aperture 61 configured between the first actuating jaw 62 and the second jaw 64, when the jaws are closed. This retainer aperture may provide secure retention of a filter, such as an inferior vena cava (IVC) filter or other item when the item is at least partially retained therein. The first actuating portion 40 pivots about the first pivot 46.

Figure 48:
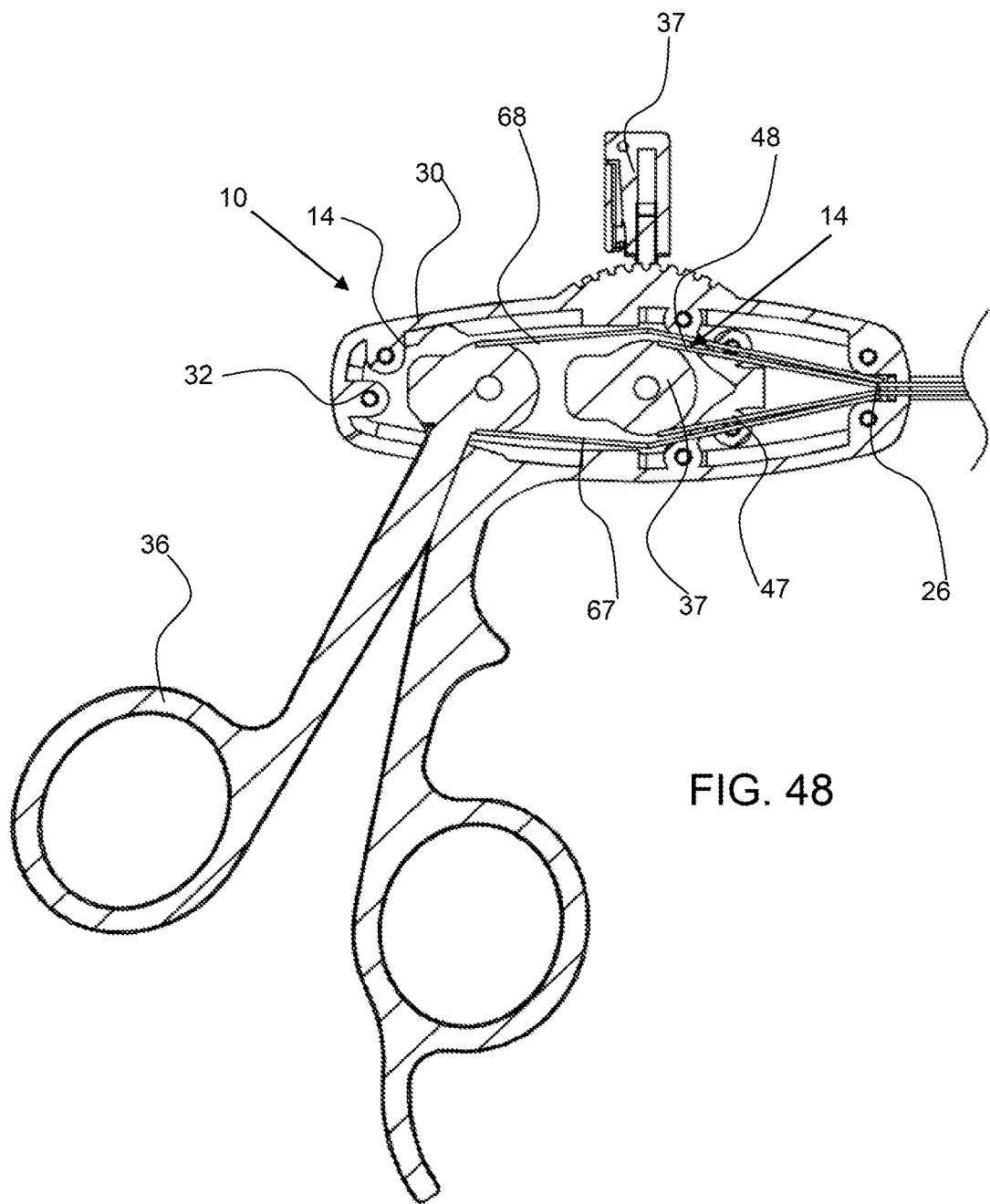
FIG. 48 shows a cross-sectional view of view of the exemplary articulating retrieval apparatus along line 48-48 of FIG. 47.

As shown in FIG. 48, a cross-sectional view of the exemplary actuating retrieval apparatus 12, shows the interior actuators, or actuating assembly 14. The first manipulator 37 is coupled with the first actuator 34 to move a first actuating portion (not shown in FIG. 28). The first actuating portion is moved by manipulating a manipulator to pull on one of first actuating portion first line 47 or first actuating portion second line 48. The retrieval implement is controlled by the retrieval actuator 36 that pulls on one of the first retrieval line 67 or second retrieval line 68.

Figures 49, 50:
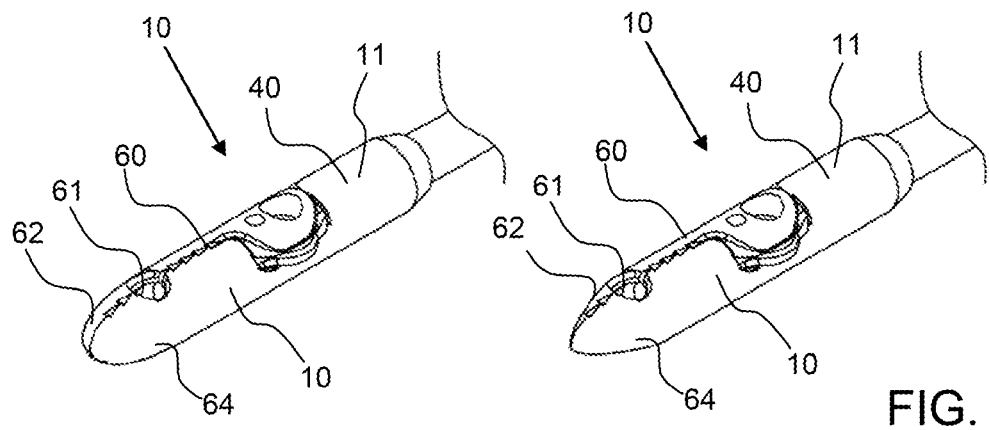
FIGS. 49 to 52 show perspective views of exemplary articulating forceps.

Referring to FIGS. 49 to 50, an exemplary articulating retrieval apparatus 10 has forceps forming a retainer aperture 61 between the first actuating jaw 62 and the second jaw 64, which may also be an actuating jaw, when the jaws are closed. This retainer aperture may provide secure retention of a foreign article for retrieval from the body, such as an IVC filter.

Figures 51, 52:
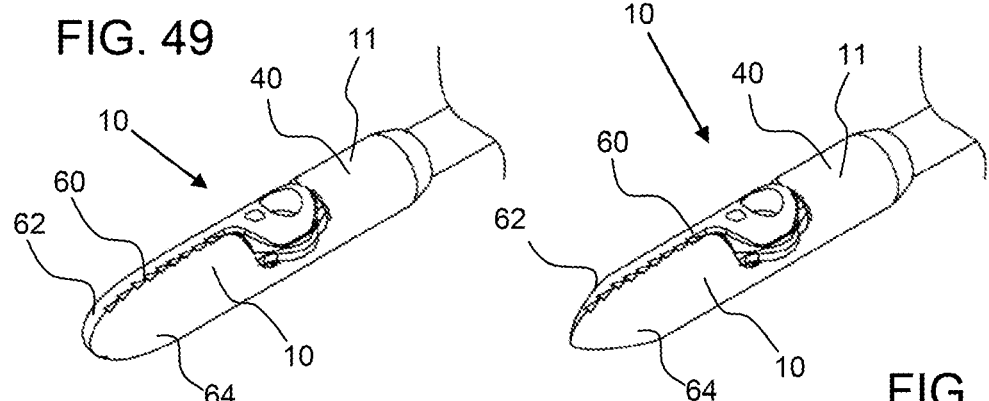

Referring to FIGS. 51 to 52, an exemplary articulating retrieval apparatus 10 has forceps without a retainer aperture between the first actuating jaw 62 and the second jaw 64 when the jaws are closed. This type of forceps may be used for retrieval by gripping a foreign object between the forceps jaws.

Figures 53, 54:
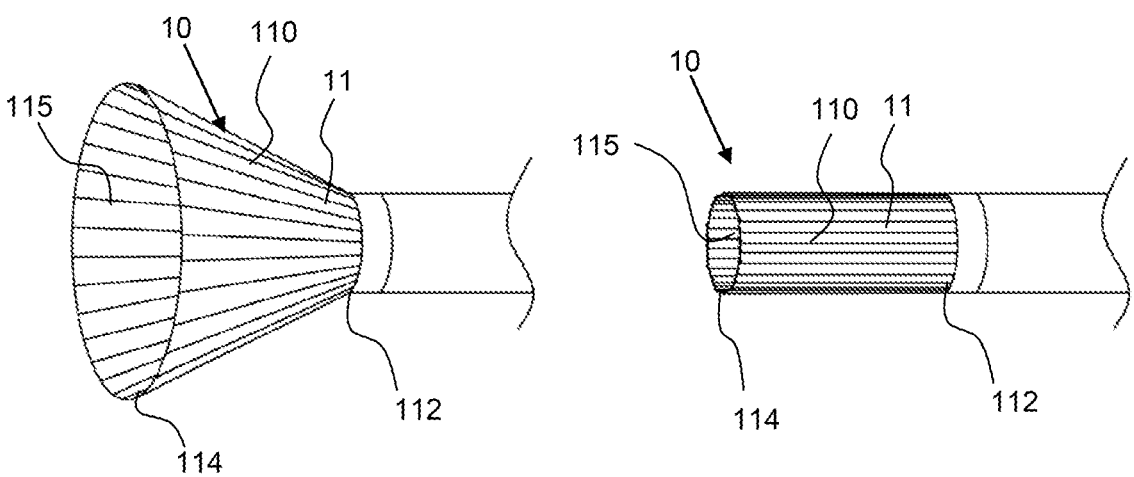
FIGS. 53 and 54 shows perspective views of an exemplary expanding funnel sheath.

Referring to FIGS. 53 and 54, an exemplary retrieval implement 11, an expandable funnel sheath 110, is configured to open up, or expand as shown in FIG. 53, wherein the extended end 114 is enlarged over the coupled end 112. The sheath forms a cylinder that can expand radially out to increase the diameter of the extended end 114 as shown in FIG. 53, and retract or collapse radially to reduce the diameter of the extended end, as shown in FIG. 54. The expandable funnel sheath is funnel shaped in an expanded configuration wherein the sheath tapers down toward the coupled end. A foreign object may be configured with the expandable funnel sheath or within the opening 115 of the expandable funnel sheath and then the expandable funnel sheath may be closed to retain the foreign object within the retracted expandable funnel sheath.

Figures 55, 56:
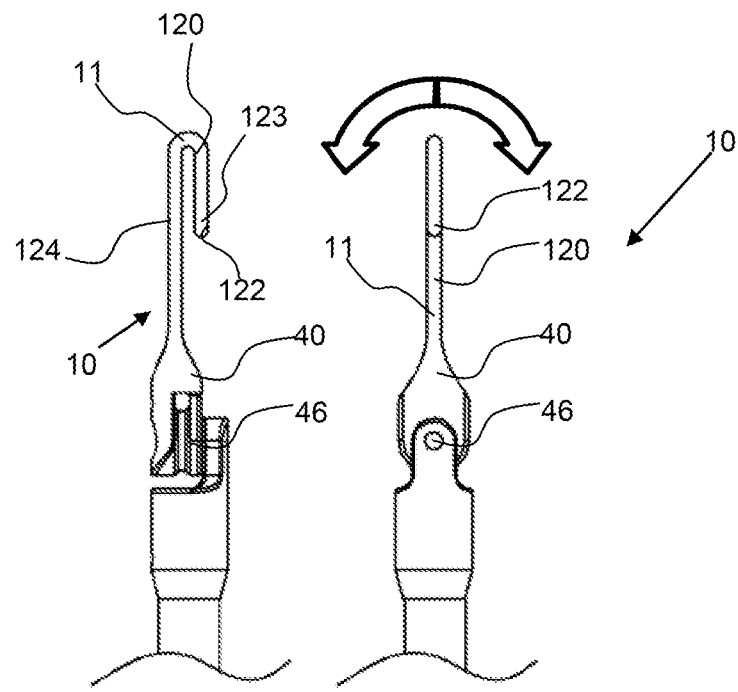
FIG. 55 shows a side view of an exemplary actuating hook.
FIG. 56 shows a top view of an exemplary actuating hook.

Referring to FIGS. 55 and 56, an exemplary retrieval implement 11, an actuating hook 120, forms a hook shape that can be manipulated by the first actuating portion 40. The hook portion 123 turns back from the hook arm 124. A hook portion turns at least 120 degrees back from the hook arm and as shown turns back about 180 degrees from the hook arm in this embodiment. A foreign object may be secured in the slot formed by the hook portion and retrieved from the body.

Figures 57, 58, 59, 60:
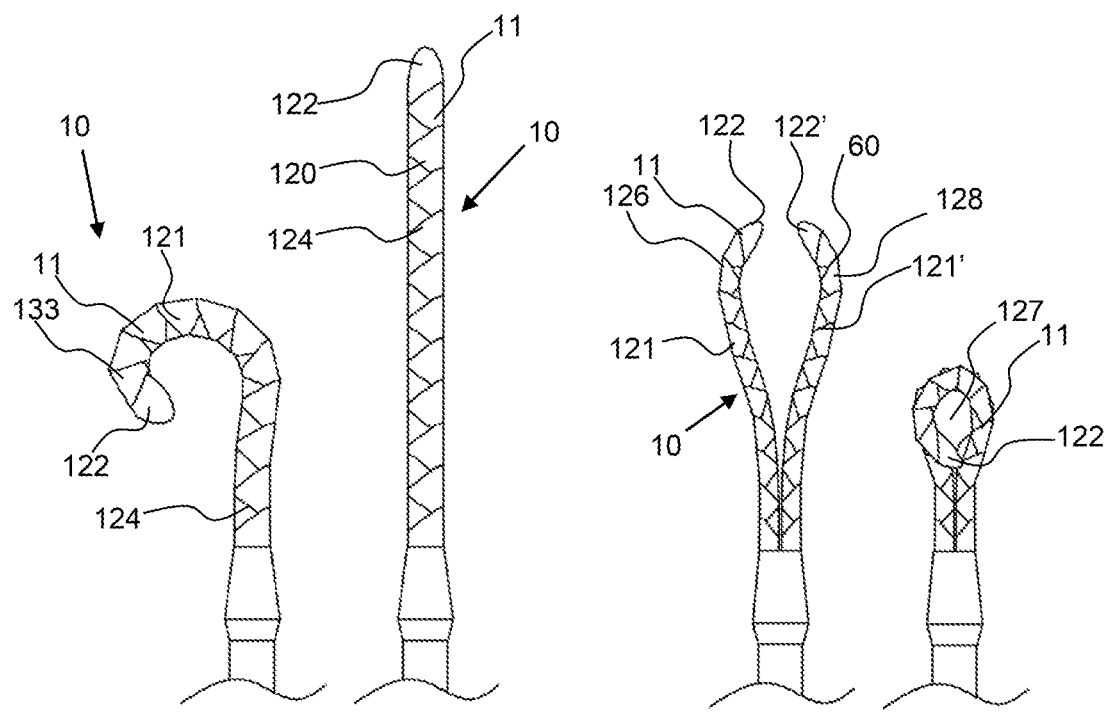
FIG. 57 shows a side view of an exemplary coil hook in a coiled configuration.
FIG. 58 shows a side view of the exemplary coil hook shown in FIG. 57, in an extended configuration.
FIG. 59 shows a side view of an exemplary dual coil hook in an extended configuration a coiled configuration.
FIG. 60 shows a side view of the exemplary coil hook shown in FIG. 58, in a coiled configuration forming a coil hoop between the two coil hooks.

Referring to FIGS. 57 and 60, an exemplary retrieval implement 11, an exemplary coil hook 121 is manipulated from a extended configuration, FIG. 58, to a coiled or hook configuration, FIG. 57. The retrieval line, as shown in FIG. 3, may be coupled with coil hook 121 proximal to the extended end 122, whereby creating tension in the retrieval line causes the coil hook to coil to form the coil hook as shown. The extended end coils backward over the coil arm 124 to form a hook, or coil. The coiled portion 133 may be used for retrieval of a foreign object from the body. As shown in FIGS. 59 and 60, an exemplary retrieval implement 11 comprise a pair of coil hooks 121, 121'. The first articulating hook 126 and the second articulating hook 128 are configured to form a coil hoop 127, or enclosed area between the two coiled hooks when in a coiled configuration. This type of implement may very positively retain a foreign object for removal from the body.

Figure 61:
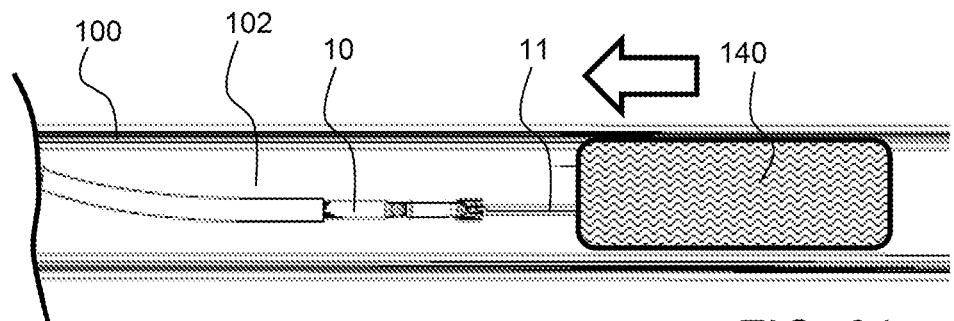
FIGS. 61 and 62 show an actuating retrieval apparatus moving a stent and stent graft.
Figure 62:
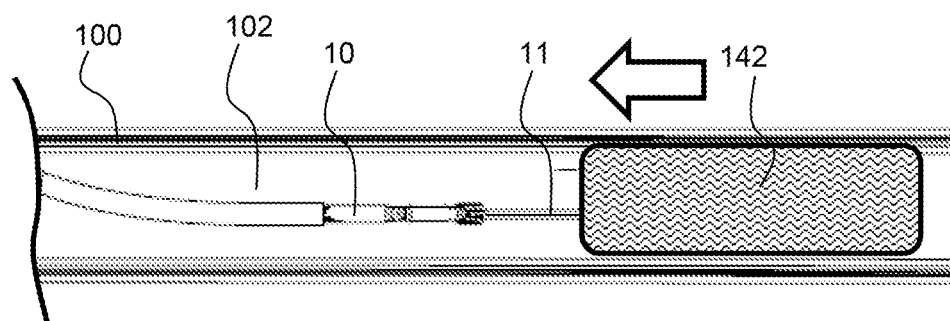

As shown in FIGS. 61 and 62 an actuating retrieval apparatus 10 is moving a stent 140 and stent graft 142, respectively.

Figure 63:
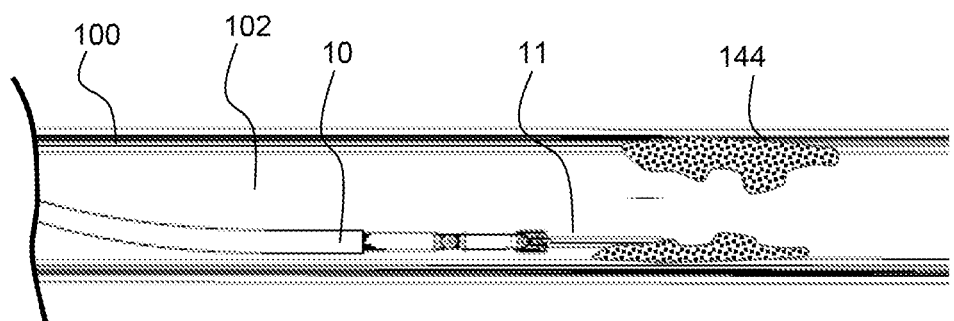
FIG. 63 show an actuating retrieval apparatus removing thrombus.

As shown in FIG. 63, an actuating retrieval apparatus 10 removing thrombus 144 with the retrieval implement 11.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. An Intravascular articulated and actuating retrieval apparatus comprising:
   a) a mechanical user interface on an interface end;
   b) catheter coupled to and extending from the user interface, said catheter comprising:
      i) user end coupled to the user interface;
      ii) a distal end; and
      iii) an apparatus conduit extending from the user end to the distal end;
   c) a first actuating portion coupled to the distal end of the apparatus conduit and comprising a first pivot,
   d) a retrieval implement coupled to the first actuating portion and comprising a first retrieval implement portion:
      said user interface comprising:
      i) a first actuator configured to actuate the first actuating portion to rotate about said first pivot; and
      ii) a retrieval actuator configured to actuate said first retrieval implement portion from an open position to a closed position;
   e) a first actuating portion first line extending from the first actuating portion to the first actuator and through the apparatus conduit;
   f) a retrieval line extending from the retrieval implement to the retrieval actuator and through the apparatus conduit;
   g) a first actuating portion second line extending from the first actuating portion to the first actuator and through the apparatus conduit;
   wherein the first actuator comprises a first manipulator coupled to the first actuating portion first line and the first actuating portion second line;
   wherein rotation of the first manipulator in a first manipulator direction pulls the first actuating portion first line to rotate the first actuating portion about the first pivot a first rotational direction and wherein rotation of the first manipulator in a second manipulator direction, opposite the first manipulator direction, pulls the first actuating portion second line to rotate the first actuating portion about the first pivot a second rotational direction, opposite the first rotational direction;
   h) a second actuating portion coupled to the first actuating portion by a second pivot;
   wherein the second actuating portion is distal the first actuating portion and wherein the user interface comprises a second actuator configured to actuate the second actuating portion to rotate about said second pivot;
   i) a second actuating portion first line extending from the second actuating portion to the second actuator and through the apparatus conduit;
   wherein the second actuator comprises a second manipulator coupled to the second actuating portion first line, wherein rotation of said second manipulator in a first manipulator direction pulls the second actuating portion first line to rotate the second actuating portion about the second pivot a first rotational direction;
   j) a second actuating portion second line extending from the second actuating portion to the second actuator and through the apparatus conduit,
   wherein the second manipulator is coupled to the second actuating portion second line, wherein rotation of the second manipulator in a second manipulator direction, opposite the first manipulator direction, pulls the second actuating portion second line to rotate the second actuating portion about the second pivot a second rotational direction, opposite the first rotational direction.

2. The Intravascular articulated and articulating retrieval apparatus of claim 1, wherein the first manipulator is a paddle.

3. The Intravascular articulated and articulating retrieval apparatus of claim 2, wherein the rotational axis of the paddle is orthogonal to the length axis of the apparatus conduit.

4. The Intravascular articulated and articulating retrieval apparatus of claim 1, wherein the second actuating portion rotates orthogonally to the first actuating portion.

5. The Intravascular articulated and articulating retrieval apparatus of claim 1, wherein the second manipulator is a second paddle.

6. The Intravascular articulated and articulating retrieval apparatus of claim 1, wherein the rotational axis of the second paddle is orthogonal to the length axis of the apparatus conduit.

7. The Intravascular articulated and articulating retrieval apparatus of claim 1, wherein the first manipulator is a first dial and the second manipulator is a second dial.

8. The Intravascular articulated and articulating retrieval apparatus of claim 7, wherein the first dial is coupled to a first worm gear and wherein the first actuating portion first line is coupled to the first worm gear and wherein the second dial is coupled to a second worm gear and wherein the second actuating portion first line is coupled to the second worm gear.

9. The Intravascular articulated and articulating retrieval apparatus of claim 8, wherein the first actuating portion second line is coupled to the first worm gear and wherein the second actuating portion second line is coupled to the second worm gear.

10. The Intravascular articulated and articulating retrieval apparatus of claim 1, wherein the first manipulator is a paddle.

11. The Intravascular articulated and articulating retrieval apparatus of claim 10, wherein the rotational axis of the paddle is orthogonal to the length axis of the apparatus conduit.

12. The Intravascular articulated and articulating retrieval apparatus of claim 1, wherein the first manipulator is a dial.

13. The Intravascular articulated and articulating retrieval apparatus of claim 1, wherein the apparatus conduit outer diameter is no more than 20 French.

14. The Intravascular articulated and articulating retrieval apparatus of claim 1, wherein the apparatus conduit outer diameter is no more than 18 French.

15. The Intravascular articulated and articulating retrieval apparatus of claim 1, wherein the apparatus conduit outer diameter is no more than 10 French.

16. The Intravascular articulated and articulating retrieval apparatus of claim 1,
wherein the retrieval actuator comprises a retrieval manipulator coupled to the retrieval line, wherein manipulation of the retrieval manipulator in a first direction moves the first retrieval implement portion to a closed position;
wherein the retrieval implement is a forceps comprising:
i) a first actuating jaw coupled to a jaw pivot; and
ii) a second jaw.

17. The Intravascular articulated and articulating retrieval apparatus of claim 16, wherein at least one of the jaws has a serrated edge.

18. The Intravascular articulated and articulating retrieval apparatus of claim 16, wherein both the first and second jaws have a serrated edge.

19. The Intravascular articulated and articulating retrieval apparatus of claim 16, wherein the forceps comprises at least one jaw that has a blade edge.

20. The Intravascular articulated and articulating retrieval apparatus of claim 16, wherein the first and second jaws form a retainer aperture in a closed position.

21. The Intravascular articulated and articulating retrieval apparatus of claim 16, wherein the forceps is a scissor jaw wherein at least one of the first or second jaws has a blade edge and wherein the first and second jaws are configured to extend past each other and overlap in a closed position.

22. The Intravascular articulated and articulating retrieval apparatus of claim 1, wherein the retrieval implement is a tweezer jaws; and wherein the tweezer jaws have extended ends that extend past each other and overlap in a closed position.

23. The Intravascular articulated and articulating retrieval apparatus of claim 1, wherein the retrieval implement is an expandable funnel sheath comprising:
a) an extended end forming an opening into said expandable funnel sheath; and
b) a coupled end coupled to the apparatus conduit;
wherein the expandable funnel sheath is manipulated by the retrieval line to open and close, wherein in an open position, the expandable funnel sheath tapers from the extended end towards the coupled end and wherein in a closed position the extended end is collapsed radially inward.

24. The Intravascular articulated and articulating retrieval apparatus of claim 1, wherein the retrieval implement is a hook.

* * * * *